United States Patent
Berthel et al.

(10) Patent No.: US 7,262,297 B2
(45) Date of Patent: *Aug. 28, 2007

(54) DIAMINOPYRROLOQUINAZOLINES COMPOUNDS AS PROTEIN TYROSINE PHOSPHATASE INHIBITORS

(75) Inventors: Steven Joseph Berthel, Mendham Township, NJ (US); Adrian Wai-Hing Cheung, Glen Rock, NJ (US); Kyungjin Kim, Livingston, NJ (US); Kshitij Chhabilbhai Thakkar, Nutley, NJ (US); Weiya Yun, Warren, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 236 days.

This patent is subject to a terminal disclaimer.

(21) Appl. No.: 10/836,507

(22) Filed: Apr. 30, 2004

(65) Prior Publication Data

US 2004/0235872 A1    Nov. 25, 2004

Related U.S. Application Data

(60) Provisional application No. 60/470,803, filed on May 15, 2003, provisional application No. 60/563,584, filed on Apr. 19, 2004.

(51) Int. Cl.
*C07D 239/00* (2006.01)
*C07D 487/00* (2006.01)

(52) U.S. Cl. .................. 544/249; 544/250

(58) Field of Classification Search ............. 547/247, 547/228.8, 267; 544/249, 250
See application file for complete search history.

(56) References Cited

U.S. PATENT DOCUMENTS

| | | | |
|---|---|---|---|
| 4,451,466 A | 5/1984 | Horne et al. | |
| 6,110,962 A | 8/2000 | Wrobel et al. | |
| 6,121,271 A | 9/2000 | Dollings et al. | |
| 2004/0229890 A1* | 11/2004 | Berthel et al. ............ | 514/267 |

FOREIGN PATENT DOCUMENTS

WO    WO 02/068425    9/2002

OTHER PUBLICATIONS

Moeller et al., Current Opinion in Drug Discovery and Development, 3, pp. 527-540 (2000).
Zhang, Zhong-Yin, Current Opinion in Chemical Biology, 5, pp. 416-423 (2001).
Martin et al., Acta Chemica Scandinavica, 47, pp. 221-230 (1993).
Suzuki, Akira, Pure and Appl. Chem., 57, pp. 1749-1758 (1985).
Ansel et al., Pharmaceutical Dosage Forms and Drug Delivery Systems, (6th Ed.) pp. 196 (1995).
Zhang et al., Expert Opin. Investig. Drugs, 12, pp. 223-233 (2003).
Suzuki et al., Synthetic Communications, 11, pp. 513-519 (1981).
Suzuki et al., Chem. Rev., 95, pp. 2457-2483 (1995).
Shieh et al., J. Org. Chem., 57, pp. 379-381 (1992).
Stille, John K., Agnew. Chem. Int. Ed. Engl., 25, pp. 508-524 (1986).

* cited by examiner

*Primary Examiner*—Alton Pryor
(74) *Attorney, Agent, or Firm*—George W. Johnston; Dennis P. Tramaloni

(57) ABSTRACT

The invention relates to pyrimido[5,4-e][1,2,4]triazine-5,7-diamine compounds which are useful for inhibiting protein tyrosine phosphatases, particularly PTP1B, and are useful for lowering blood glucose concentrations in mammals.

59 Claims, No Drawings

DIAMINOPYRROLOQUINAZOLINES COMPOUNDS AS PROTEIN TYROSINE PHOSPHATASE INHIBITORS

PRIORITY TO PROVISIONAL APPLICATION(S) UNDER 35 U.S.C. §119(e)

This application claims priority under 35 U.S.C. §119(e) of provisional application(s) Ser. No. 60/470,803, filed May 15, 2003 and Ser. No. 60/563,584, filed Apr. 19, 2004.

FIELD OF THE INVENTION

The invention relates to diaminopyrroloquinazolines compounds useful for inhibiting protein tyrosine phosphatases, particularly PTP1B, and are useful for lowering blood glucose concentrations in mammals.

BACKGROUND OF THE INVENTION

Protein tyrosine phosphatases (PTPases) are key enzymes in processes that regulate cell growth and differentiation. The inhibition of these enzymes can play a role in the modulation of multiple signaling pathways in which tyrosine phosphorylation dephosphorylation plays a role. PTP1B is a particular protein tyrosine phosphatases that is often used as a prototypical member of that class of enzymes.

PTPase inhibitors are recognized as potential therapeutic agents for the treatment of diabetes. See, e.g. Moeller et al., 3(5):527-40, Current Opinion in Drug Discovery and Development, 2000; or Zhang, Zhong-Yin, 5:416-23, Current Opinion in Chemical Biology, 2001. The utility of PTPase inhibitors as therapeutic agents has been a topic of discussion in several review articles including, for example, Expert Opin Investig Drugs, 12(2):223-33, Feb. 2003.

SUMMARY OF THE INVENTION

It has been discovered that compounds of the formula:

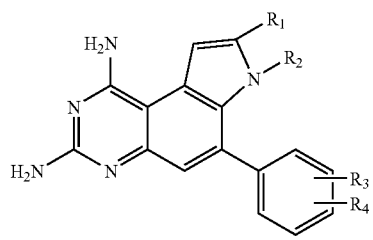

I-A wherein
$R_1$ is selected from hydrogen and lower alkyl;
$R_2$ is selected from the group consisting of hydrogen, lower alkyl,

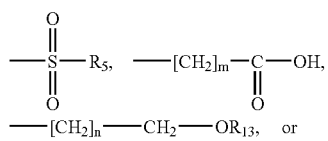

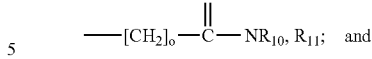

$R_3$ and $R_4$ are independently selected from the group consisting of hydrogen, lower alkyl, lower alkenyl, lower alkoxy, hydroxy lower alkyl, perfluoroloweralklyl, nitro, halo, lower alkanoyl, —N $R_5R_6$, $R_7S$—,

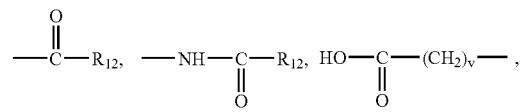

phenyl, hydroxy, perfluoroloweralkoxy, and phenoxy, or
$R_3$ and $R_4$ when present on adjacent carbon atoms on the phenyl ring can be taken together with their adjacent carbon atoms to form a lower alkylenedioxy bridge or an aromatic ring system fused to the phenyl ring, said aromatic ring system containing one or two aromatic rings with one of said rings being either an aromatic or heteroaromatic ring;
$R_5$ and $R_6$ are independently selected from hydrogen and lower alkyl;
$R_{12}$ is selected from the group consisting of hydrogen, benzyl, phenyl and lower alkyl;
$R_7$ is lower alkyl;
$R_{13}$ is selected from the group consisting of hydrogen, lower alkyl, benzyl and phenyl;
$R_{10}$, $R_{11}$ and $R_{12}$ are independently selected from hydrogen and lower alkyl; and
m, n, o and v are independent integers selected from 0 to 4,
or pharmaceutically acceptable salts thereof,
inhibit protein tyrosine phosphatases, particularly PTP1B and are therefore useful for lowering blood glucose concentrations in mammals.

In another embodiment, it has also been discovered that compounds of the formula:

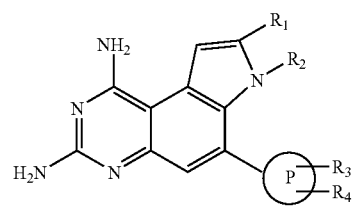

I-B wherein
Ⓟ is a 5 or 6 membered heteroaromatic ring containing from 1 to 2 hetero atoms selected from the group consisting of oxygen, sulfur, and nitrogen;
R1 is selected from hydrogen and lower alkyl;
$R_2$ is selected from the group consisting of hydrogen, lower alkyl,

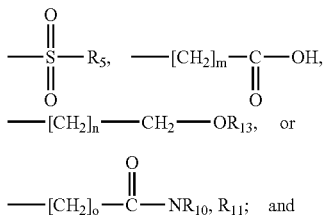

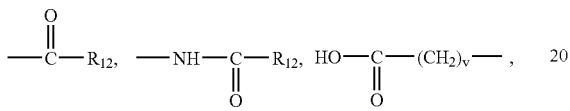

$R_3$ and $R_4$ are independently selected from the group consisting of hydrogen, lower alkyl, lower alkenyl, lower alkoxy, hydroxy lower alkyl, perfluoroloweralklyl, nitro, halo, lower alkanoyl, —N $R_5R_6R_7S$—,

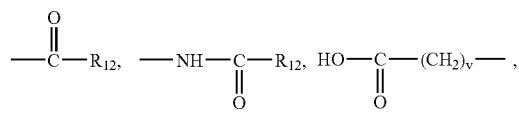

phenyl, hydroxy, perfluoroloweralkoxy, and phenoxy, or
$R_3$ and $R_4$ when present on adjacent carbon atoms on the heteroaromatic ring can be taken together with their adjacent carbon atoms to form a lower alkylenedioxy bridge or an aromatic ring system fused to the phenyl ring, said aromatic ring system containing one or two aromatic rings with one of said rings being either an aromatic or heteroaromatic ring;

$R_5$ and $R_6$ are independently selected from hydrogen and lower alkyl;

$R_2$ is selected from the group consisting of hydrogen, benzyl, phenyl and lower alkyl;

$R_7$ is lower alkyl;

$R_{13}$ is selected from the group consisting of hydrogen, lower alkyl, benzyl and phenyl;

$R_{10}$, $R_{11}$ and $R_{12}$ are independently selected from hydrogen and lower alkyl; and m, n, o and v are independent integers selected from 0 to 4, or pharmaceutically acceptable salts thereof, inhibit protein tyrosine phosphatases, particularly PTP1B and are therefore useful for lowering blood glucose concentrations in mammals.

DETAILED DESCRIPTION OF THE INVENTION

The present invention comprises compounds of the formula:

I-A

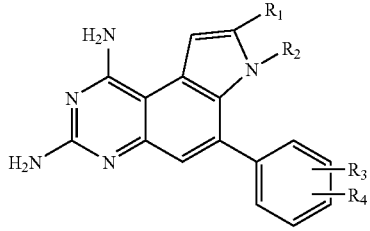

wherein
$R_1$ is selected from hydrogen and lower alkyl;

$R_2$ is selected from the group consisting of hydrogen, lower alkyl,

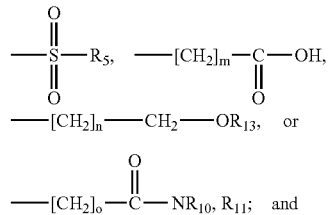

$R_3$ and $R_4$ are independently selected from hydrogen, lower alkyl, lower alkenyl, lower alkoxy, hydroxy lower alkyl, perfluoroloweralklyl, nitro, halo, lower alkanoyl, —N $R_5R_6$, $R_7S$—,

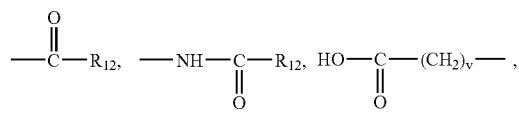

phenyl, hydroxy, perfluoroloweralkoxy, and phenoxy, or
$R_3$ and $R_4$ when present on adjacent carbon atoms on the phenyl ring can be taken together with their adjacent carbon atoms to form a lower alkylenedioxy bridge or an aromatic ring system fused to the phenyl ring, said aromatic ring system containing one or two aromatic rings with one of said rings being either an aromatic or heteroaromatic ring;

$R_5$ and $R_6$ are independently selected from hydrogen and lower alkyl;

$R_{12}$ is selected from the group consisting of hydrogen, benzyl, phenyl and lower alkyl;

$R_7$ is lower alkyl;

$R_{13}$ is selected from the group consisting of hydrogen, lower alkyl, benzyl and phenyl;

$R_{10}$, $R_{11}$, and $R_{12}$ are independently selected from hydrogen and lower alkyl; and m, n, o and v are independent integers selected from 0 to 4, or pharmaceutically acceptable salts thereof, inhibit protein tyrosine phosphatases, particularly PTP1B and are therefore useful for lowering blood glucose concentrations in mammals.

Another embodiment of the compounds of this invention comprises compounds of the formula:

I-B

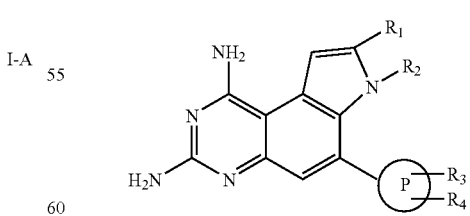

wherein
Ⓟ is a 5 or 6 membered heteroaromatic ring containing from 1 to 2 hetero atoms selected from the group consisting of oxygen, sulfur, and nitrogen;
R1 is selected from hydrogen and lower alkyl;

$R_2$ is selected from the group consisting of hydrogen, lower alkyl,

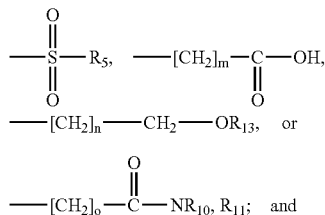

$R_3$ and $R_4$ are independently selected from the group consisting of hydrogen, lower alkyl, lower alkenyl, lower alkoxy, hydroxy lower alkyl, perfluoroloweralklyl, nitro, halo, lower alkanoyl, —N $R_5R_6R_7S$—,

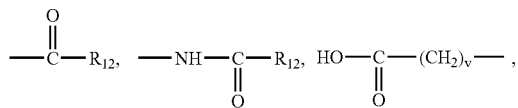

phenyl, hydroxy, perfluoroloweralkoxy, and phenoxy, or $R_3$ and $R_4$ when present on adjacent carbon atoms on the heteroaromatic ring can be taken together with their adjacent carbon atoms to form a lower alkylenedioxy bridge or an aromatic ring system fused to the phenyl ring, said aromatic ring system containing one or two aromatic rings with one of said rings being either an aromatic or heteroaromatic ring;

$R_5$ and $R_6$ are independently selected from hydrogen and lower alkyl;

$R_2$ is selected from the group consisting of hydrogen, benzyl, phenyl and lower alkyl;

$R_7$ is lower alkyl;

$R_{13}$ is selected from the group consisting of hydrogen, lower alkyl, benzyl and phenyl;

$R_{10}$, $R_{11}$, and $R_{12}$ are independently selected from hydrogen and lower alkyl; and m, n, o and v are independent integers selected from 0 to 4, or pharmaceutically acceptable salts thereof, inhibit protein tyrosine phosphatases, particularly PTP1B and are therefore useful for lowering blood glucose concentrations in mammals.

As used in the specification, the term "lower alkyl", alone or in combination, means a straight-chain or branched-chain alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means an unsubstituted or substituted 3- to 7-membered saturated carbocyclic ring.

The term lower "alkoxy" means a straight-chain or branched-chain alkoxy group containing from one to six carbon atoms, such as methoxy, ethoxy, n-propoxy, isopropoxy, n-butoxy, tert-butoxy and the like.

The term "heteroaromatic" means a mono-cyclic heteroaromatic ring or a fused ring system containing one or more hetero atoms in the ring system such as nitrogen atom, oxygen atom and sulphur atom within the ring or ring system. Examples of "heteroaryl group" are pyridyl group, thienyl group and furyl.

The term "aryl" means a mono- or bicyclic aromatic group, such as phenyl or naphthyl, which is unsubstituted or substituted by conventional substituent groups.

The term "lower alkylenedioxy" denotes a divalent saturated hydrocarbon moiety containing from one to six carbon atoms having terminal oxygens which are placed at the end of the lower alkylene chain and connect to the rest of the molecule. The preferred lower alkylenedioxy moieties are 1,2-ethylene dioxy, methylene dioxy, 1,3-propylene dioxy. Generally, the preferred lower alkylene dioxy moieties are formed in a straight chain.

The term "pharmaceutically acceptable salts" refers to conventional acid-addition salts or base-addition salts that retain the biological effectiveness and properties of the compounds of formulas I, II, III and IV and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

The preferred compounds of the Compounds of Formula I-A and I-B above are those compounds where $R_1$ is hydrogen. Particularly preferred among those classes of compounds where $R_1$ is hydrogen are those compounds where $R_2$ is hydrogen or lower alkyl.

There are many different embodiments of the compounds of formula I-A. The main embodiments of the compounds of formula I-A are first, those compounds where $R_3$ and $R_4$ are present on the phenyl ring on the compound of formula I-A on adjacent carbon atoms and taken together form a lower alkylene dioxy bridge. The second major embodiment are those compounds of formula I-A where $R_3$ and $R_4$ are present on adjacent carbon atoms on the phenyl ring and are taken together with their adjacent carbon atoms to form an aromatic ring system fused to the phenyl ring. The third major embodiment are those compounds where $R_3$ and $R_4$ are individual, connected to the phenyl ring.

In the first embodiment where $R_3$ and $R_4$ form a lower alkylenedioxy bridge, these bridges preferably contain from one to three carbon atoms. In a preferred class of this embodiment, $R_2$ is hydrogen or lower alkyl and $R_1$ is hydrogen or lower alkyl, preferably hydrogen.

The second major embodiment of the compounds of formula I-A are those compounds where $R_3$ and $R_4$ are substituted on adjacent carbon atoms and taken together with their attached carbon atoms form a fused aromatic ring system containing from 1 to 3 fused rings fused to the phenyl ring on the compound of formula I-A. One class of compounds in this embodiment are those compounds where the fused aromatic ring system, fused to the phenyl ring on the compound of formula I-A, can contain one hetero aromatic ring and/or one hetero aromatic and/or one aromatic ring. In the embodiment where $R_3$ and $R_4$ form a fused aromatic ring system, $R_1$ is preferably hydrogen and $R_2$ is preferably hydrogen or lower alkyl. In this second major embodiment of the compounds of formula I-A, another class of compounds are those compounds where $R_3$ and $R_4$ when taken together with their attached carbon atoms form a single fused heteroaromatic ring or an aromatic ring such as phenyl. In this embodiment $R_1$ and $R_2$ are preferably hydrogen or lower alkyl. In this second major embodiment of the compounds of formula I-A, another class of compounds are those compounds where $R_3$ and $R_4$ when taken together with their attached carbon atoms form a two membered fused ring system which is fused to the phenyl group on the compound of formula I. These two membered ring systems can be both aromatic rings or one hetero aromatic ring and one aromatic ring.

In the third major embodiment, $R_3$ and $R_4$ are independent groups separately attached to the phenyl moiety in the compound of formula I-A. One of the compounds within this embodiment include compounds where $R_1$ and $R_2$ are independently hydrogen or lower alkyl and $R_3$ and $R_4$ are independently hydrogen, lower alkyl or lower alkenyl. In this preferred group of compounds, lower alkenyl denotes a monovalent aliphatic hydrocarbon substituent containing from two to six carbon atoms and having an unsubstituted double bond within its structure. The preferred group of compounds where $R_4$ is lower alkenyl are compounds where $R_3$ is hydrogen and $R_1$ and $R_2$ are independently hydrogen or lower alkyl.

Another class of compounds within the compounds of formula I-A where $R_3$ and $R_4$ are independent substituents are those compounds where $R_3$ and $R_4$ are individually hydrogen, halogen, trifluoroloweralkyl, preferably trifluoromethyl, and trifluoroloweralkoxy, preferably trifluoromethoxy, with one of $R_3$ and $R_4$ being other than hydrogen. Within this class of compounds are those compounds where $R_1$ and $R_2$ are either hydrogen or lower alkyl.

Another class of compounds within the embodiment of $R_3$ and $R_4$ being individual separate substituents are those compounds where $R_3$ is hydrogen or halogen and $R_4$ is halogen, nitro, lower alkoxy, phenoxy, hydroxy or hydroxyalkyl. Among this class of compounds, compounds where $R_1$ and $R_2$ are hydrogen or lower alkyl are preferred. In another class of compounds within this embodiment, where $R_3$ is halogen or hydrogen, another class of compounds are those where $R_4$ is:

v is an integer from 0 to 4;
$R_{12}$ is hydrogen or lower alkyl. In this embodiment, $R_4$ can be either an aldehyde, where $R_{12}$ is H or a ketone where $R_{12}$ is lower alkyl. Also in this regard, $R_3$ and $R_4$ can form one or two lower carboxylic acid groups.

In accordance with another embodiment of the compound of formula I-A where $R_3$ and $R_4$ are independent substituents, there are those compounds where $R_1$ and $R_2$ are independently hydrogen or lower alkyl; $R_3$ and $R_4$ are hydrogen, $R_7S$—, $R_5R_6N$—, or

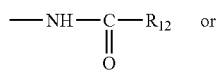

$R_5$ and $R_6$ are independently hydrogen or lower alkyl;

$R_7$ is lower alkyl; and
one of $R_3$ and $R_4$ is other than hydrogen.

Furthermore, in accordance with the embodiment of this invention where $R_3$ and $R_4$ in the compound of formula I-A are independent substituents are those class of compounds where $R_2$ is

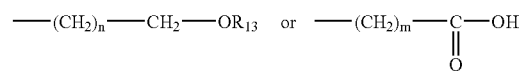

$R_{13}$ is hydrogen, phenyl, benzyl or lower alkyl; and
m and n is an integer from 0 to 4. In this case $R_1$ is generally hydrogen or lower alkyl, preferably hydrogen. In addition, $R_3$ and $R_4$ can be halogen or trifluoroalkyl, preferably trifluoromethyl with one of $R_3$ and $R_4$ being halogen or hydrogen.

In another class of compounds where $R_3$ and $R_4$ are separate independent substituents are those compounds where $R_2$ is

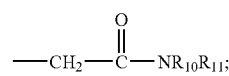

$R_{10}$ and $R_{11}$ are independently hydrogen or lower alkyl. In this group of compounds, R1 is hydrogen or lower alkyl, preferably hydrogen. Also, with respect to this class of compounds, $R_3$ and $R_4$ are preferably hydrogen or lower alkoxy.

The compound of formula I-B contains various different embodiments in the same manner as the compound of formula I-A. The first major embodiment are those compounds where $R_3$ and $R_4$ taken together form a lower alkylene dioxy bridge. The second are those compounds where $R_3$ and $R_4$ taken together with their adjacent carbon atoms to form an aromatic ring system which contains one or two aromatic or heteroaromatic rings fused to the heteroaromatic ring (P) in the compound of formula I-B. On the other hand, in accordance with a third embodiment of this invention, the compound of $R_3$ and $R_4$ on the compound of formula I-B can be independent, individual substituents. The embodiments formed in this manner are the same as set forth with regard to compounds I-A.

In addition, since the compound of formula I-B contains within its structure a heteroaromatic ring, this heteroaromatic ring can contain sulfur, oxygen or nitrogen as the only hetero atom. On the other hand, this structure can contain two hetero atoms with each being the same or each being a different hetero atom such as oxygen or nitrogen. One such embodiment of those compounds, where the hetero aromatic ring contains sulfur as the only hetero atom. In this embodiment, the class of compounds where $R_3$ and $R_4$ are independently halogen or lower alkyl are preferred. In addition, those class of compounds where $R_3$ and $R_4$ are independently hydrogen, halogen or lower alkyl and $R_1$ and $R_2$ are hydrogen and lower alkyl are especially preferred.

In addition, with respect to those compounds of formula I-B where the hetero aromatic ring in this compound contains the sulfur atom as the only hetero atom in its ring, the class of compounds where $R_3$ and $R_4$ is hydrogen, or

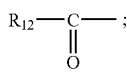

$R_{12}$ is hydrogen or lower alkyl; and $R_3$ and $R_4$ is other than hydrogen are preferred. In this embodiment, those compounds where $R_1$ and $R_2$ are hydrogen and lower alkyl are especially preferred.

As indicated hereinabove, $R_3$ and $R_4$ which are present when attached on adjacent carbon atoms on the hetero aromatic ring can be taken together with their attached carbon atoms to form a fused ring system. This ring system can be either a hetero aromatic ring or an aromatic ring. The preferred fused aromatic ring is a phenyl ring.

This invention is also directed to a pharmaceutical composition comprising one or more compounds of formulas I-A and I-B.

Moreover, this invention is directed to a method of treating a disease based on high blood glucose concentration comprising administering to a patient in need of such treatment a therapeutically effective amount of at least one compound of the formulas I-A and I-B.

The compounds of the invention can exist as stereoisomers and diastereomers, all of which are encompassed within the scope of the present invention.

The compounds of the invention inhibit PTP1B in vitro and have been shown to lower blood glucose levels in vivo. Thus, the compounds of the present invention would be useful for the treatment of diabetes.

The compounds of the invention can be administered orally, rectally, or parentally, e.g., intravenously, intramuscularly, subcutaneously, intrathecally or transdermally; or sublingually, or as opthalmalogical preparations. Capsules, tablets, suspensions or solutions for oral administration, suppositories, injection solutions, eye drops, salves or spray solutions are examples of administration forms.

Intravenous, intramuscular, oral or inhalation administration are preferred forms of use. The dosages in which the compounds of the invention are administered in effective amount depend on the nature of the specific active ingredient, the age and requirements of the patient and the mode of administration. Dosages may be determined by any conventional means, e.g., by dose-limiting clinical trials. In general, dosages of about 0.1 to 100 mg/kg body weight per day are preferred, with dosages of 1-25 mg/kg per day being particularly preferred.

The invention further comprises pharmaceutical compositions that contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and Oral unit dosage forms, such as tablets and capsules, preferably contain from 25 mg to 1000 mg of a compound of the invention. The compounds of the invention may be prepared by any conventional means.

In accordance with this invention, the compounds herein as well as their pharmaceutically acceptable salts are useful in the control or prevention of illnesses associated with high blood glucose concentration. A preferred indication associated with the present invention is that associated with diabetes.

The dosage can vary within wide limits and will, of course, have to be adjusted to the individual requirements in each particular case. In the case of oral administration, the dosage for adults may vary from about 0.01 mg to about 1000 mg per day of a compound of formula I-A and I-B or of the corresponding amount of a pharmaceutically acceptable salt thereof. The daily dosage may be administered as single dose or in divided doses, and in addition, the upper limit can also be exceeded when this is found to be indicated.

A particular method is described in the following Schemes 1 and 2. The examples following each of the schemes provide a detailed description of the schematic methods. In the following reaction schemes Ⓐ designates a phenyl ring or Ⓟ which is a heteroaromatic ring. In the following schemes, $R_8$ and $R_9$ are the same as $R_3$ and $R_4$.

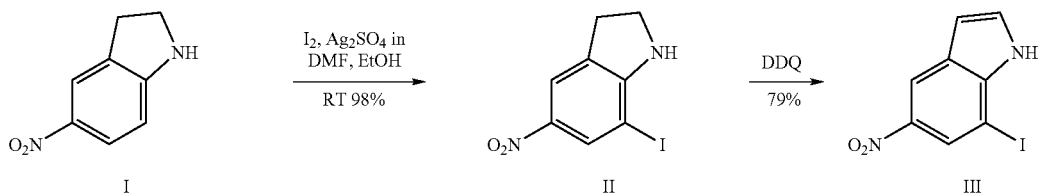

1. Fe, NH$_4$Cl in MeOH/H$_2$O
2. HCl in MeO quant

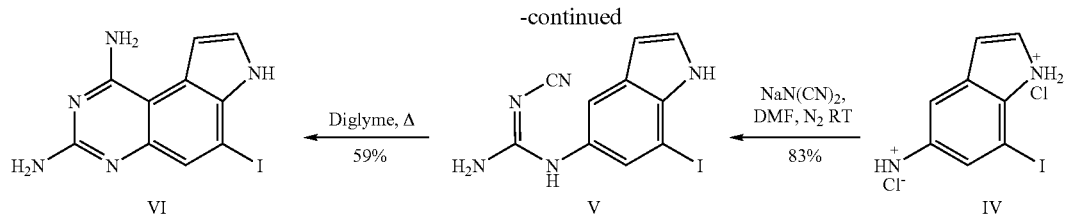

Compound II: A mixture of silver sulfate (100 g, 0.32 mol) and iodine (82 g, 0.32 mol) in N,N-dimethylformamide (700 mL) and ethanol (1400 mL) was treated with 5-nitro-2,3-dihydro-1H-indole I (48 g, 0.29 mol). The resulting mixture was stirred at 25° C. for 1.5 h, filtered and the filter pad washed with ethyl acetate. The filtrate was concentrated in vacuo to a volume of approximately 500 mL. This solution was treated with a 1.0N aqueous sodium thiosulfate solution (100 mL) and a saturated aqueous sodium chloride solution (400 mL). The resulting precipitate was collected by filtration, washed with water and petroleum ether, and dried in vacuo to afford 7-iodo-5-nitro-2,3-dihydro-1H-indole II (83.9 g, 98.9%) as a white solid: $^1$H NMR (DMSO-$d_6$, 300 MHz) δ 8.18 (d, J=2.20 Hz, 1H), 7.80 (d, J=1.46 Hz, 1H), 7.03 (broad s, 1H) 3.65 (t, J=8.97 Hz, 2H), 3.17 (t, J=8.60 Hz, 2H).

Compound III: A solution of 7-iodo-5-nitro-2,3-dihydro-1H-indole II (15 g, 51.7 mmol) in ethanol (1200 mL) and isopropanol (20 mL) at 25° C. was treated with 2,3-dichloro-5,6-dicyano-1,4-benzoquinone (13.6 g, 59.9 mmol). The resulting solution was warmed to 65° C. and air was bubbled through for 1 h. An additional 0.57 equivalents of 2,3-dichloro-5,6-dicyano-1,4-benzoquinone (6.8 g, 29.9 mmol) was added and the reaction was stirred at 65° C. for another 2 h before being concentrated in vacuo. Flash chromatography (Merck Silica gel 60, 230-400 mesh, 90/10 toluene/ethyl acetate) afforded 7-iodo-5-nitro-1H-indole III (13.07 g, 79%) as a yellow solid: $^1$H NMR (DMSO-$d_6$, 300 MHz) δ 11.82 (broad s, 1H), 8.59 (d, J=1.83 Hz, 1H), 8.30 (d, J=1.83 Hz, 1H), 7.61 (t, J=2.93 Hz, 1H), 6.90 (dd, $J_1$=1.83 Hz, $J_2$=3.30 Hz, 1H).

Compound IV: A solution of 7-iodo-5-nitro-1H-indole III (20 g, 69.4 mmol) in methanol (650 mL) at 25° C. was treated with a solution of ammonium chloride (26.1 g, 485.8 mmol) in water (550 mL) and iron powder (13.6 g, 242.9 mmol). The mixture was heated to 100° C. under a nitrogen atmosphere for 5 h. The resulting mixture was filtered through a pad of celite and the celite pad washed with hot methanol. The filtrate was concentrated in vacuo and the residue was partitioned between methylene chloride and water and separated. The pH of the aqueous layer was adjusted to pH=10 with ammonium hydroxide and extracted with methylene chloride. The combined organic layers were dried over sodium sulfate, filtered, and concentrated in vacuo to a volume of 250 mL. This solution was treated with a 4.0M aqueous hydrochloric acid solution in dioxane and stirred at 25° C. for 2 h. The precipitate was collected by filtration and washed with methylene chloride and petroleum ether to afford 7-iodo-1H-indol-5-ylamine hydrochloride IV (24.7 g, quant.) as a gray solid: $^1$H NMR (DMSO-$d_6$, 300 MHz) δ 11.34 (broad s, 1H), 9.93 (broad s, 2H), 7.56 (d, J=1.46 Hz, 1H), 7.48 (t, J=2.74 Hz, 1H), 7.44 (d, J=1.83 Hz, 1H), 6.68 (dd, $J_1$=1.83 Hz, $J_2$=2.93 Hz, 1H).

Compound V: A solution of 7-iodo-1H-indol-5-ylamine hydrochloride IV (24.6 g, 83.7 mmol) in N,N-dimethylformamide (400 mL) at 25° C. was treated with sodium dicyanamide (18.6 g, 209 mmol). The reaction mixture was warmed to 50° C. for 2 h, concentrated in vacuo, and the residue treated with water (500 mL). The resulting mixture was allowed to stand at 25° C. for 2.5 h during which time a yellow precipitate formed. The precipitate was collected by filtration and washed with water to afford N"-cyano-N-(7-iodo-1H-indol-5-yl)guanidine V (22.59 g, 83%) as a light yellow solid: $^1$H NMR (DMSO-$d_6$, 300 MHz) δ 11.02 (broad s, 1H), 8.89 (broad s, 1H), 7.46 (d, J=1.83 Hz, 1H), 7.37 (d, J=1.83 Hz, 1H), 7.35 (t, J=2.56 Hz, 1H), 6.85 (broad S, 2H), 6.56(dd, $J_1$=1.83 Hz, $J_2$=3.10 Hz, 1H).

Compound VI: A solution of N"-cyano—N-(7-iodo-1H-indol-5-yl)guanidine V (6.0 g, 18.7 mmol) in 2-methoxyethyl ether (50 mL) was heated to 175° C. for 32.5 h. The reaction mixture was cooled to 25° C., the resulting solids removed by filtration and washed with methanol. The filtrate was concentrated in vacuo to give a brown oil. The residue was dissolved in methanol and then absorbed onto Merck Silica gel 60, 230-400 mesh (25 g). Flash chromatography (Merck Silica gel 60, 230-400 mesh, 90/10/1 methylene chloride/methanol/ammonium hydroxide) afforded 6-iodo-7H-pyrrolo[3,2-f]quinazoline-1,3-diamine VI (3.61 g, 59%) as a brown solid: $^1$H NMR (DMSO-$d_6$, 300 MHz) δ 11.36 (broad s, 1H), 7.45 (broad s, 1H), 7.43 (t, J=2.93 Hz, 1H), 7.20 (s, 1H), 6.74 (broad s, 2H), 5.78 (broad s, 2H).

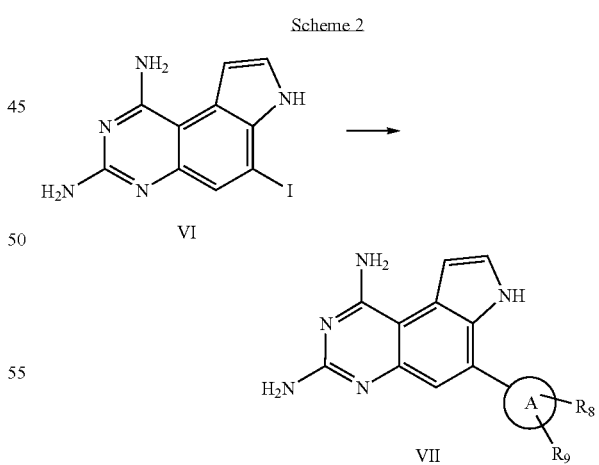

Scheme 2

Compound VII: The coupling reaction can be carried out by a conventional aryl coupling method, e.g., Suzuki coupling method: (a) Suzuki et al., *synth.commun.* 1981, 11, 513, (b) Suzuki *pure and Appl. Chem.* 1985, 57, 1749-1758, (c) Suzuki et al., *Chem. Rev.* 1995, 95,2457-2483, (d) Shieh et al., *J. Org. Chem.* 1992,57,379-381, (e) Martin et al., *Acta Chemica Scandinavica.* 1993, 47, 513.

Typical conditions used to carry out the Suzuki coupling of 6-iodo-7H-pyrrolo[3,2-f]quinazoline-1,3-diamine VI includes the use of either aryl or heteroaromatic boronic acid or esters (e.g., where Ar is defined as aryl) as coupling partner, in aqueous base such as sodium bicarbonate or potassium carbonate or barium hydroxide or triethylamine solution, a palladium catalyst (2-20 mole %) such as tetrakis (triphenylphosphine)-palladium (0) or [1,1'bis(diphenylphosphino)-ferrocene]dichloro-palladium(II), in a suitable solvent such as aqueous ethanol or THF or DMF or ethylene glycol for at temperatures ranging from 25° C. to 125° C. for 2-18 hr yields compound VII.

Alternatively, coupling reaction can be carried out by a conventional aryl or heteroaromatic coupling partner utilizing Stille coupling, e.g., Stille et al., *Angew. Chem. Int. Ed. Engl.,* 1986,25,508.

Typical conditions used to carry out the Stille reaction include the use of an organostannane as the coupling partner, palladium catalyst (2-20 mole %) such as tetrakis(triphenylphosphine)-palladium (0) or [1,1'bis(diphenylphosphino)-ferrocene]dichloro-palladium(II), a salt such as potassium fluoride or lithium chloride, in a suitable anhydrous solvent such as THF or DMF or ethylene glycol for at temperatures ranging from 25° C. to 125° C. for 2-18 hr yields compound VII.

Compound VIII: A solution of 6-iodo-7H-pyrrolo[3,2-f]quinazoline-1,3-diamine VI, 400 mg, 1.23 mmol) in tetrahydrofuran (20 mL) at 25° C. was treated with sodium hydroxide (98 mg, 2.46 mmol), methyl iodide (0.09 mL, 1.48 mmol), and tetrabutylammonium bromide (198 mg, 0.62 mmol), and the resulting mixture stirred at 25° C. for 18 h. The reaction mixture was treated with ethyl acetate, water, and a saturated aqueous sodium chloride solution, shaken and separated. The aqueous layer was extracted with ethyl acetate, and the combined organic layers were dried over sodium sulfate, filtered, and concentrated in vacuo to afford 6-iodo-7-methyl-7H-pyrrolo[3,2-f]quinazoline-1,3-diamine (500 mg) as a yellow solid. The product was taken on into the next reaction without further purification 6-iodo-7-methyl-7H-pyrrolo[3,2-f]quinazoline-1,3-diamine VIII.

Compound IX: The coupling reaction can be carried out by a conventional aryvl coupling method, e.g., Suzuki coupling method: (a) Suzuki et al., *synth.commun.* 1981, 11, 513, (b) Suzuki *pure and Appl. Chem.* 1985, 57, 1749-1758, (c) Suzuki et al., *Chem. Rev.* 1995, 95,2457-2483, (d) Shieh et al., *J. Org. Chem.* 1992,57,379-381, (e) Martin et al., *Acta Chemica Scandinavica.* 1993, 47,513.

Typical conditions used to carry out the Suzuki coupling of VIII includes the use of either aryl or heteroaromatic boronic acid or esters (e.g., where Ar is defined as aryl) as coupling partner, in aqueous base such as sodium bicarbonate or potassium carbonate or barium hydroxide or triethylamine solution, a palladium catalyst (2-20 mole %) such as tetrakis(triphenylphosphine)-palladium (0) or [1,1'-bis(diphenylphosphino)-ferrocene]dichloro-palladium(II), in a suitable solvent such as aqueous ethanol or THF or DMF or ethylene glycol for at temperatures ranging from 25° C. to 125° C. for 2-18 hr yields 6-Aryl-7-methyl-7H-pyrrolo[3,2-f]quinazoline-1,3-diamine X.

Alternatively, coupling reaction can be carried out by a conventional aryl or heteroaromatic coupling partner utilizing Stille coupling, e.g., Stille et al., *Angew. Chem. Int. Ed. Engl.,* 1986, 25, 508.

Typical conditions used to carry out the Stille reaction include the use of an organostannane as the coupling partner, palladium catalyst (2-20 mole %) such as tetrakis(triphenylphosphine)-palladium (0) or [1,1'bis(diphenylphosphino)-ferrocene]dichloro-palladium(II), a salt such as potassium fluoride or lithium chloride, in a suitable anhydrous solvent such as THF or DMF or ethylene glycol for at temperatures ranging from 25° C. to 125° C. for 2-18 hr yields compound 6-Aryl-7-methyl-7H-pyrrolo[3,2-f]quinazoline-1,3-diamine IX.

Scheme 3

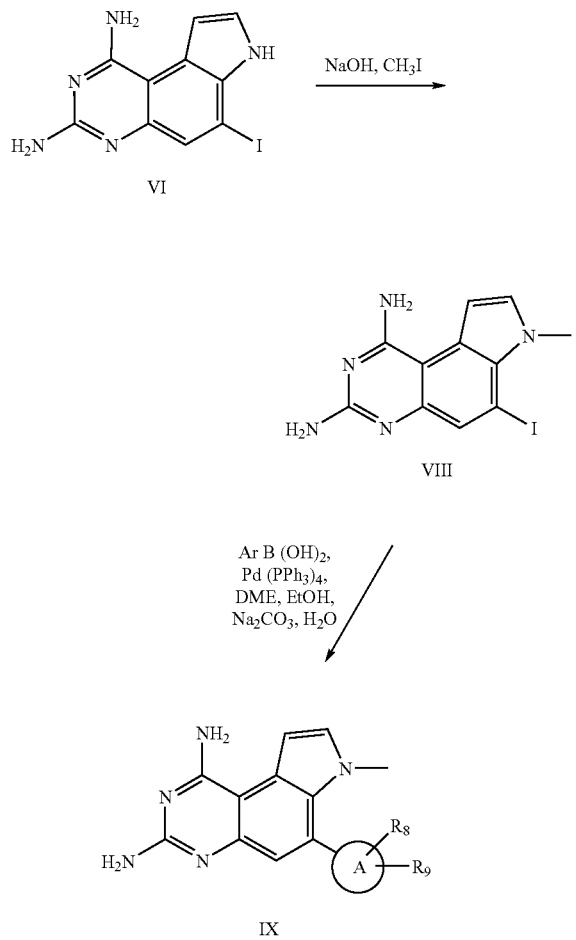

Scheme 4:

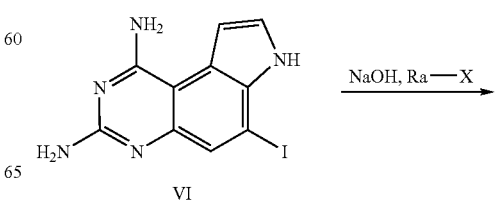

-continued

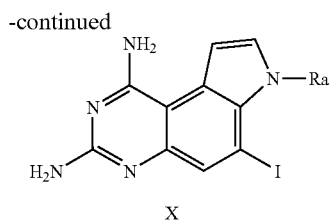

X

Ar B (OH)₂,
Pd (PPh₃)₄,
DME, EtOH,
Na₂CO₃, H₂O
↓

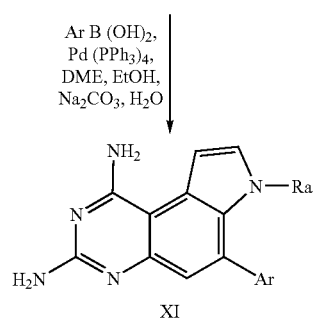

XI

Compound X: Typical condition used to carry out alkylation of 6-iodo-7H-pyrrolo[3,2-f]quinazoline-1,3-diamine VI and phase transfer catalyst such as tetrabutylammonium bromide, with variety of halides (e.g. RaBr or RaI, where Ra is defined above) is carried out with suitable solvent such as tetrahydrofuran, DMF using suitable base such as sodium hydroxide at temperatures ranging from −78° C. to 25° C. to provide the 6-iodo-7-alkyl-7H-pyrrolo[3,2-f]quinazoline-1,3-diamine XI.

6-Aryl-7-alkyl-7H-pyrrolo[3,2-f]quinazoline-1,3-diamine XI: The coupling reaction can be carried out by a conventional aryl coupling method, e.g., Suzuki coupling method: (a) Suzuki et al., *synth.commun.* 1981, 11, 513, (b) Suzuki, *Pure and Appl. Chem.* 1985, 57, 1749-1758, (c) Suzuki et al., *Chem. Rev.* 1995, 95, 2457-2483, (d) Shieh et al., *J. Org. Chem.* 1992, 57, 379-381, (e) Martin et al., *Acta Chemica Scandinavica.* 1993, 47, 513.

Typical conditions used to carry out the Suzuki coupling of 6-iodo-7-alkyl-7H-pyrrolo[3,2-f]quinazoline-1,3-diamine X includes the use of either aryl or heteroaromatic boronic acid or esters (e.g. where Ar is defined as aryl) as coupling partner, in aqueous base such as sodium bicarbonate or potassium carbonate or barium hydroxide or triethylamine solution, a palladium catalyst (2-20 mole %) such as tetrakis(triphenylphosphine)-palladium (0) or [1,1'bis(diphenylphosphino)-ferrocene]dichloro-palladium(II), in a suitable solvent such as aqueous ethanol or THF or DMF or ethylene glycol for at temperatures ranging from 25° C. to 125° C. for 2-18 hr yields compound X.

Alternatively, coupling reaction can be carried out by a conventional aryl or heteroaromatic coupling partner utilizing Stille coupling. e.g., Stille et al., *Angew. Chem. Int. Ed. Engl.,* 1986, 25, 508.

Typical conditions used to carry out the Stille reaction include the use of an organostannane as the coupling partner, palladium catalyst (2-20 mole%) such as tetrakis(triphenylphosphine)-palladium (0) or [1,1'bis(diphenylphosphino)-ferrocene]dichloro-palladium(II), a salt such as potassium fluoride or lithium chloride, in a suitable anhydrous solvent such as THF or DMF or ethylene glycol for at temperatures ranging from 25° C. to 125° C. for 2-18 hr yields 6-Aryl-7-alkyl-7H-pyrrolo[3,2-f]quinazoline-1,3-diamine XI.

This invention is illustrated by the following Examples. In the Examples, the procedures of Examples 2-28 were carried out by the procedure of Example 1. In the Examples, the procedures of Examples 30-33 were carried out by the procedure of Example 29. In the Examples, the procedures of Examples 35-104 were carried out by the procedure of Example 34. In the Examples, the procedures of Examples 106-112 were carried out by the procedure of Example 105. In the Examples, the procedure of Example 114 was carried out by the procedure of Example 113.

EXAMPLES

Example 1

6-(3,5-Bis-trifluoromethyl-phenyl)-7H-pyrrolo[3,2-f]quinazoline-1,3-diamine

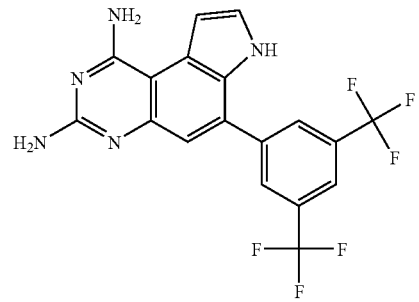

A solution of 6-iodo-7H-pyrrolo[3,2-f]quinazoline-1,3-diamine (322 mg, 0.99 mmol) in ethylene glycol dimethyl ether (3.0 mL) and ethanol (3.0 mL)at 25° C. was treated with 3,5-bis(trifluoromethyl)benzene boronic acid (510 mg, 1.98 mmol), a saturated aqueous sodium bicarbonate solution (1.5 mL), and tetrakis(triphenylphosphine)-palladium (0) (115 mg, 0.1 mmol). The resulting mixture was heated to 80° C. for 18 h, cooled, filtered and the isolated solids washed with ethyl acetate. The filtrate was pre-absorbed onto silica gel and purified by flash chromatography (Merck Silica gel 60, 230-400 mesh, 90/10/1 methylene chloride/methanol/ammonium hydroxide) to give 6-(3,5-bis-trifluoromethyl-phenyl)-7H-pyrrolo[3,2-f]quinazoline-1,3-diamine (218 mg, 53.5%) as a yellow solid; EI-HRMS m/e calcd for $C_{18}H_{11}F_6N_5$ (M⁺) 411.0918. Found 411.0921.

In an analogous manner, there were obtained:

Example 2

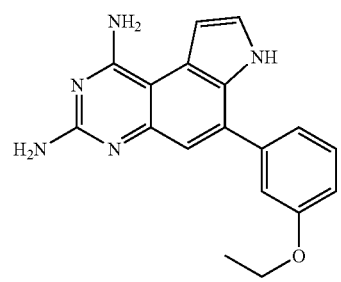

From 6-iodo-7H-pyrrolo[3,2-f]quinazoline-1,3-diamine and 3-ethoxyphenylboronic acid there was produced 6-(3-

Ethoxy-phenyl)-7H-pyrrolo[3,2-f]quinazoline-1,3-diamine trifluoro-acetic acid salt; LRMS for $C_{18}H_{17}N_5O$ (M+H)$^+$ at m/z=320.

Example 3

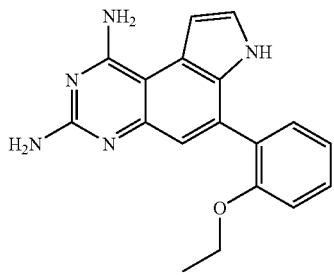

From 6-iodo-7H-pyrrolo[3,2-f]quinazoline-1,3-diamine and 2-ethoxyphenylboronic acid there was produced 6-(2-Ethoxy-phenyl)-7H-pyrrolo[3,2-f]quinazoline-1,3-diamine trifluoro-acetic acid salt; LRMS for $C_{18}H_{17}N_5O$ (M+H)$^+$ at m/z=320.

Example 4

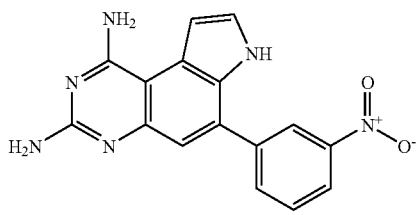

From 6-iodo-7H-pyrrolo[3,2-f]quinazoline-1,3-diamine and 3-nitrophenylboronic acid there was produced 6-(3-Nitro-phenyl)-7H-pyrrolo[3,2-f]quinazoline-1,3-diamine; EI-HRMS m/e calcd for $C_{16}H_{12}N_6O_2$ (M$^+$) 320.1022. Found 320.1020.

Example 5

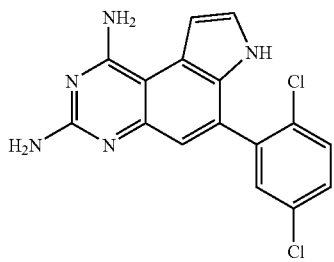

From 6-iodo-7H-pyrrolo[3,2-f]quinazoline-1,3-diamine and 2,5-dichlorophenylboronic acid there was produced 6-(2,5-Dichloro-phenyl)-7H-pyrrolo[3,2-f]quinazoline-1,3-diamine; EI-HRMS m/e calcd for $C_{16}H_{11}Cl_2N_5$ (M$^+$) 343.0391. Found 343.0392.

Example 6

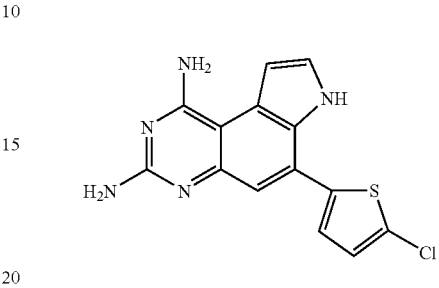

From 6-iodo-7H-pyrrolo[3,2-f]quinazoline-1,3-diamine and 5-chlorothiophene-2-boronic acid there was produced 6-(5-Chloro-thiophen-2-yl)-7H-pyrrolo[3,2-f]quinazoline-1,3-diamine trifluoro-acetic acid salt; (ES)$^+$-HRMS m/e calcd for $C_{14}H_{10}ClN_5S$ (M+H) 316.0418. Found 316.0422.

Example 7

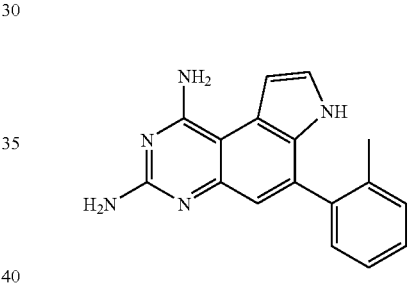

From 6-iodo-7H-pyrrolo[3,2-f]quinazoline-1,3-diamine and o-tolylboronic acid there was produced 6-o-Tolyl-7H-pyrrolo[3,2-f]quinazoline-1,3-diamine as an off-white solid; EI-HRMS m/e calcd for $C_{17}H_{15}N_5$ (M+H)$^+$ 290.1400. Found 290.1399.

Example 8

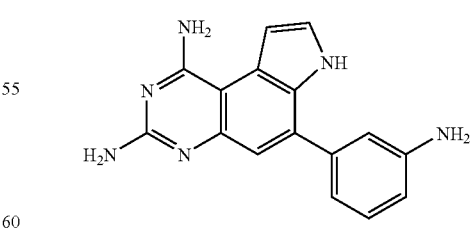

From 6-iodo-7H-pyrrolo[3,2-f]quinazoline-1,3-diamine and 3-aminobenzeneboronic acid there was produced 6-(3-Amino-phenyl)-7H-pyrrolo[3,2-f]quinazoline-1,3-diamine trifluoro-acetic acid salt as a white solid; LRMS for $C_{16}H_{14}N_6$ (M+H)$^+$ at m/z=291.

Example 9

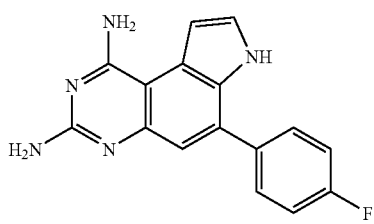

From 6-iodo-7H-pyrrolo[3,2-f]quinazoline-1,3-diamine and 4-fluorophenylboronic acid there was produced 6-(4-Fluoro-phenyl)-7H-pyrrolo[3,2-f]quinazoline-1,3-diamine trifluoro-acetic acid salt as a white solid; LRMS for $C_{16}H_{12}FN_5$ (M+H)$^+$ at m/z=294.

Example 10

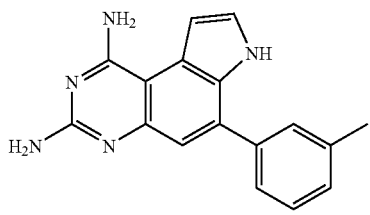

From 6-iodo-7H-pyrrolo[3,2-f]quinazoline-1,3-diamine and 3-methylphenylboronic acid there was produced 6-m-Tolyl-7H-pyrrolo[3,2-f]quinazoline-1,3-diamine trifluoro-acetic acid salt as a white solid;. LRMS for $C_{17}H_{15}N_5$ (M+H)$^+$ at m/z=290

Example 11

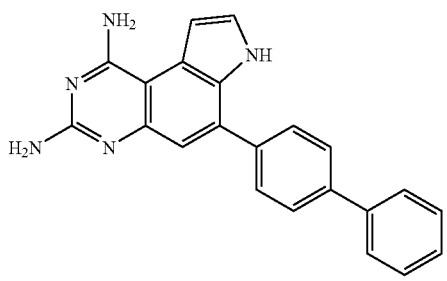

From 6-iodo-7H-pyrrolo[3,2-f]quinazoline-1,3-diamine and 4-biphenylphenylboronic acid there was produced 6-Biphenyl-4-yl-7H-pyrrolo[3,2-f]quinazoline-1,3-diamine trifluoro-acetic acid salt as a white solid; LRMS for $C_{22}H_{17}N_5$ (M+H)$^+$ at m/z=352.

Example 12

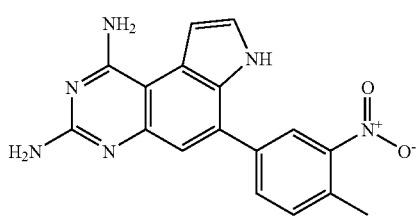

From 6-iodo-7H-pyrrolo[3,2-f]quinazoline-1,3-diamine and 4-methyl-3-nitrophenylboronic acid there was produced 6-(4-methyl-3-nitro-phenyl)-7H-pyrrolo[3,2-f]quinazoline-1,3-diamine trifluoro-acetic acid salt as a white solid; LRMS for $C_{17}H_{14}N_6O_2$ (M+H)$^+$ at m/z=335.

Example 13

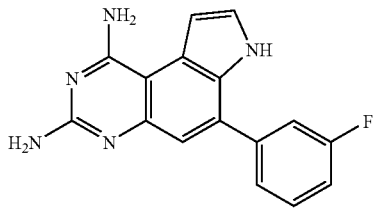

From 6-iodo-7H-pyrrolo[3,2-f]quinazoline-1,3-diamine and 3-fluorophenylboronic acid there was produced 6-(3-Fluoro-phenyl)-7H-pyrrolo[3,2-f]quinazoline-1,3-diamine trifluoro-acetic acid salt as a white solid; LRMS for $C_{16}H_{12}FN_5$ (M+H)$^+$ at m/z=294.

Example 14

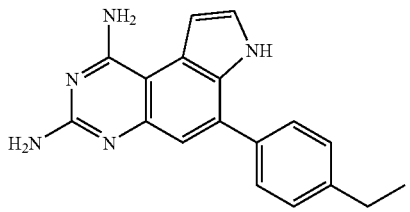

From 6-iodo-7H-pyrrolo[3,2-f]quinazoline-1,3-diamine and 4-ethylphenylboronic acid there was produced 6-(4-Ethyl-phenyl)-7H-pyrrolo[3,2-f]quinazoline-1,3-diamine trifluoro-acetic acid salt as a white solid; LRMS for $C_{18}H_{17}N_5$ (M+H)$^+$ at m/z=335.

Example 15

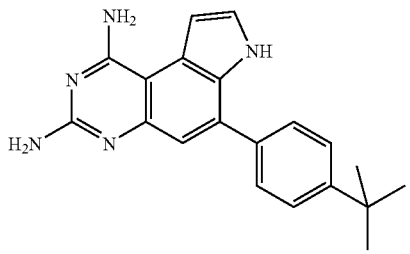

From 6-iodo-7H-pyrrolo[3,2-f]quinazoline-1,3-diamine and 4-tert-butylbenzeneboronic acid there was produced 6-(4-tert-Butyl-phenyl)-7H-pyrrolo[3,2-f]quinazoline-1,3-diamine trifluoro-acetic acid salt as a white solid; LRMS for $C_{20}H_{21}N_5$ (M+H)$^+$ at m/z=332.

Example 16

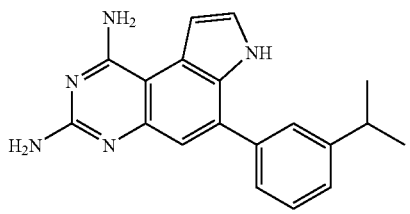

From 6-iodo-7H-pyrrolo[3,2-f]quinazoline-1,3-diamine and (3-isopropylphenyl)boronic acid there was produced 6-(3-Isopropyl-phenyl)-7H-pyrrolo[3,2-f]quinazoline-1,3-diamine trifluoro-acetic acid salt a white solid; LRMS for $C_{19}H_{19}N_5$ $(M+H)^+$ at m/z=318.

Example 17

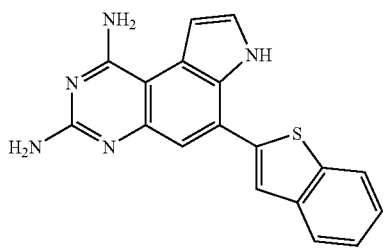

From 6-iodo-7H-pyrrolo[3,2-f]quinazoline-1,3-diamine and benzo(B)thiophene-2-boronic acid there was produced 6-Benzo[b]thiophen-2-yl-7H-pyrrolo[3,2-f]quinazoline-1,3-diamine trifluoro-acetic acid salt as white solid; LRMS for $C_{18}H_{13}N_5S$ $(M+H)^+$ at m/z=332.

Example 18

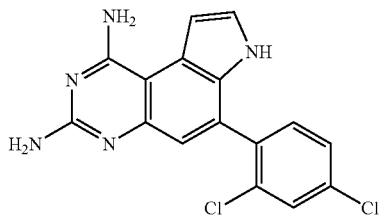

From 6-iodo-7H-pyrrolo[3,2-f]quinazoline-1,3-diamine and 2,4-dichlorophenylboronic acid there was produced 6-(2,4-Dichloro-phenyl)-7H-pyrrolo[3,2-f]quinazoline-1,3-diamine trifluoro-acetic acid salt as a white solid; LRMS for $C_{16}H_{11}Cl_2N_5$ $(M+H)^+$ at m/z=344.

Example 19

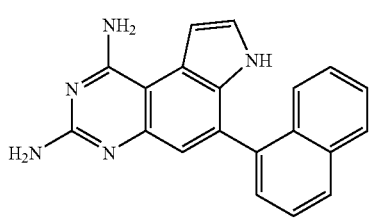

From 6-iodo-7H-pyrrolo[3,2-f]quinazoline-1,3-diamine and 1-naphthaleneboronic acid there was produced 6—Naphthalen-1-yl-7H-pyrrolo[3,2-f]quinazoline-1,3-diamine trifluoro-acetic acid salt as a white solid; LRMS for $C_{20}H_{15}N_5$ $(M+H)^+$ at m/z=326.

Example 20

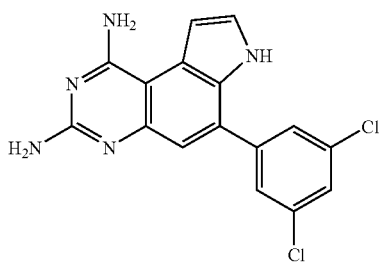

From 6-iodo-7H-pyrrolo[3,2-f]quinazoline-1,3-diamine and 3,5-dichlorophenylboronic acid there was produced 6-(3,5-Dichloro-phenyl)-7H-pyrrolo[3,2-f]quinazoline-1,3-diamine trifluoro-acetic acid salt as a white solid; LRMS for $C_{16}H_{11}Cl_2N_5$ $(M+H)^+$ at m/z=344.

Example 21

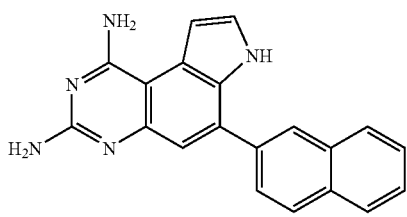

From 6-iodo-7H-pyrrolo[3,2-f]quinazoline-1,3-diamine and naphthalene-2-boronic acid there was produced 6—Naphthalen-2-yl-7H-pyrrolo[3,2-f]quinazoline-1,3-diamine trifluoro-acetic acid salt as a white solid; LRMS for $C_{20}H_{15}N_5$ $(M+H)^+$ at m/z=326.

Example 22

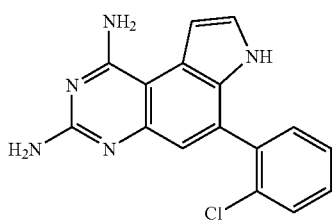

From 6-iodo-7H-pyrrolo[3,2-f]quinazoline-1,3-diamine and 2-chlorophenylboronic acid there was produced 6-(2-Chloro-phenyl)-7H-pyrrolo[3,2-f]quinazoline-1,3-diamine trifluoro-acetic acid salt as a white solid; LRMS for $C_{16}H_{12}ClN_5$ $(M+H)^+$ at m/z=310.

Example 23

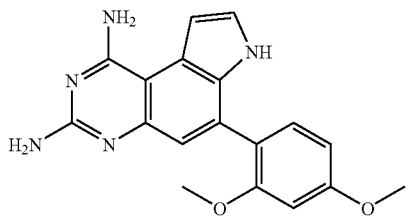

From 6-iodo-7H-pyrrolo[3,2-f]quinazoline-1,3-diamine and 2,4-dimethoxyphenylboronic acid there was produced 6-(2,4-Dimethoxy-phenyl)-7H-pyrrolo[3,2-f]quinazoline-1,3-diamine trifluoro-acetic acid salt as a white solid; LRMS for $C_{18}H_{17}N_5O_2$ (M+H)$^+$ at m/z=336.

Example 24

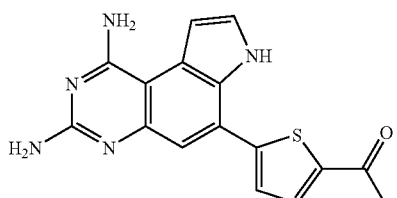

From 6-iodo-7H-pyrrolo[3,2-f]quinazoline-1,3-diamine and 5-acetyl-2-thiopheneboronic acid there was produced 1-[5-(1,3-Diamino-7H-pyrrolo[3,2-f]quinazolin-6-yl)-thiophen-2-yl]-ethanone trifluoro-acetic acid salt as a white solid; LRMS for $C_{16}H_{13}N_5OS$ (M+H)$^+$ at m/z=324.

Example 25

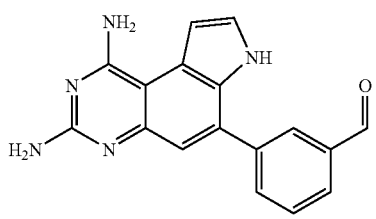

From 6-iodo-7H-pyrrolo[3,2-f]quinazoline-1,3-diamine and 3-formylphenylboronic acid there was produced 3-(1,3-Diamino-7H-pyrrolo[3,2-f]quinazolin-6-yl)-benzaldehyde as a yellow solid; (ES)$^+$-HRMS m/e calcd for $C_{17}H_{13}N_5O$ (M+H)$^+$ 304.1193. Found 304.1195.

Example 26

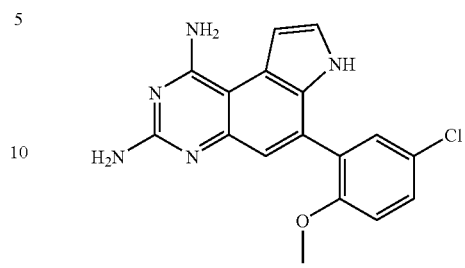

From 6-iodo-7H-pyrrolo[3,2-f]quinazoline-1,3-diamine and 5-chloro-2-methoxyphenylboronic acid there was produced 6-(5-Chloro-2-methoxy-phenyl)-7H-pyrrolo[3,2-f]quinazoline-1,3-diamine trifluoro-acetic acid salt; LRMS for $C_{17}H_{14}ClN_5O$ (M+H)$^+$ at m/z=340.

Example 27

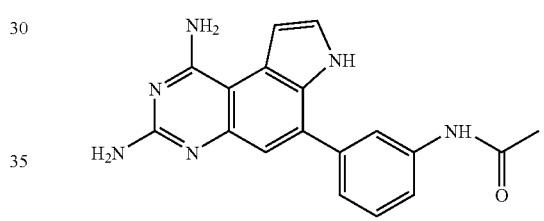

From 6-iodo-7H-pyrrolo[3,2-f]quinazoline-1,3-diamine and (3-acetylaminophenyl)boronic acid there was produced N-[3-(1,3-Diamino-7H-pyrrolo[3,2-f]quinazolin-6-yl)-phenyl]-acetamide trifluoro-acetic acid salt as a white solid; LRMS for $C_{18}H_{16}N_6O$ (M+H)$^+$ at m/z=333.

Example 28

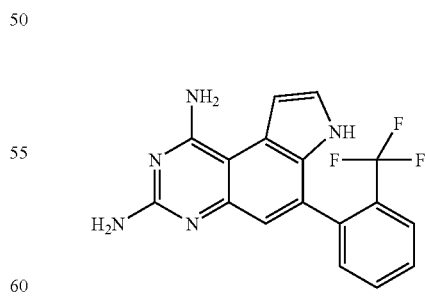

From 6-iodo-7H-pyrrolo[3,2-f]quinazoline-1,3-diamine and 2-(trifluoromethylbenzene)boronic acid there was produced 6-(2-Trifluoromethyl-phenyl)-7H-pyrrolo[3,2-f]quinazoline-1,3-diamine as a light brown solid; LRMS for $C_{17}H_{12}F_3N_5$ (M+H)$^+$ at m/z=344.

Example 29

3-[2-(1,3-Diamino-7H-pyrrolo[3,2-f]Quinazolin-6-yl)-Phenyl]-Propionic Acid

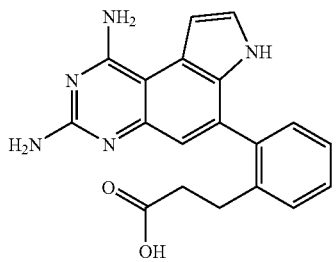

A mixture of 3-(2-bromo-phenyl)-propionic acid (458 mg, 2.0 mmol), 4,4,5,5,4',4',5',5'-octamethyl-[2,2']bi[[1,3,2]dioxaborolanyl](558 mg, 2.20 mmol), [1,1'-bis(diphenylphosphino)ferrocene]dichloropalladium (II) (132 mg, 0.18 mmol), and potassium acetate (589 mg, 6.0 mmol) was heated to 95° C. for 2 d. The resulting mixture was diluted with water and extracted with ethyl acetate. The combined organic layers were washed with a saturated aqueous sodium chloride solution, filtered through a pad of silca gel and sodium sulfate, and concentrated in vacuo to afford 3-[2-(4,4,5,5-tetramethyl-[1,3,2]dioxaborolan-2-yl)-phenyl]-propionic acid. A solution of 6-iodo-7H-pyrrolo[3,2-f]quinazoline-1,3-diamine (prepared as in Example 1, 100 mg, 0.31 mmol), 3-[2-(4,4,5,5-tetramethyl-[1,3,2]dioxaborolan-2-yl)-phenyl]-propionic acid (102 mg, 0.37 mmol), tetrakis(triphenylphosphine)palladium(o) (71 mg, 0.06 mmol) in a 2.0M aqueous sodium carbonate solution (0.5 mL), ethanol (1.5 mL), and ethylene glycol dimethyl ether (1.5 mL) was heated to 95° C. for 18 h. The resulting mixture was cooled to 25° C., dissolved in methanol and tetrahydrofuran, and filtered through a pad of silica gel and sodium sulfate. The filtrate was concentrated in vacuo. HPLC purification (Shimadzu HPLC, ODSA column from Medchem, 2×10 cm, 10 micro, 10-90% $CH_3CN/H_2O$ with 0.1% TFA.) afforded 3-[2-(1,3-diamino-7H-pyrrolo[3,2-f]quinazolin-6-yl)-phenyl]-propionic acid (12.5 mg, 12.1%); LRMS for $C_{19}H_{17}N_5O_2$ $(M+H)^+$ at m/z=348.

In an analogous manner, there were obtained:

Example 30

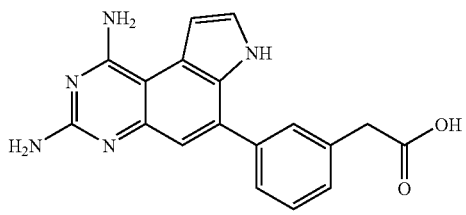

From 6-iodo-7H-pyrrolo[3,2-f]quinazoline-1,3-diamine and [3-(4,4,5,5-Tetramethyl-[1,3,2]dioxaborolan-2-yl)-phenyl]-acetic acid there was produced [3-(1,3-Diamino-7H-pyrrolo[3,2-f]quinazolin-6-yl)-phenyl]-acetic acid; LRMS for $C_{18}H_{15}N_5O_2$ $(M+H)^+$ at m/z=334.

Example 31

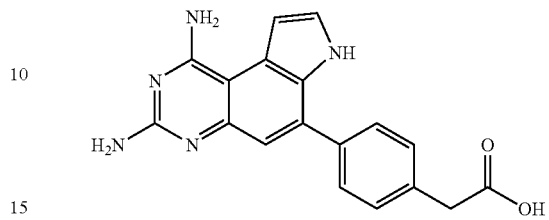

From 6-iodo-7H-pyrrolo[3,2-f]quinazoline-1,3-diamine and [4-(4,4,5,5-Tetramethyl-[1,3,2]dioxaborolan-2-yl)-phenyl]-acetic acid there was produced [4-(1,3-Diamino-7H-pyrrolo[3,2-f]quinazolin-6-yl)-phenyl]-acetic acid; LRMS for $C_{18}H_{15}N_5O_2$ $(M+H)^+$ at m/z=334.

Example 32

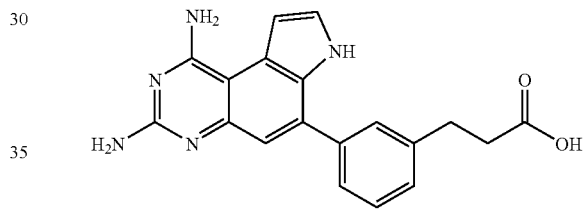

From 6-iodo-7H-pyrrolo[3,2-f]quinazoline-1,3-diamine and 3-[3-(4,4,5,5-Tetramethyl-[1,3,2]dioxaborolan-2-yl)-phenyl]-propionic acid there was produced 3-[3-(1,3-Diamino-7H-pyrrolo[3,2-f]quinazolin-6-yl)-phenyl]-propionic acid; LRMS for $C_{19}H_{17}N_5O_2$ $(M+H)^+$ for m/z=348.

Example 33

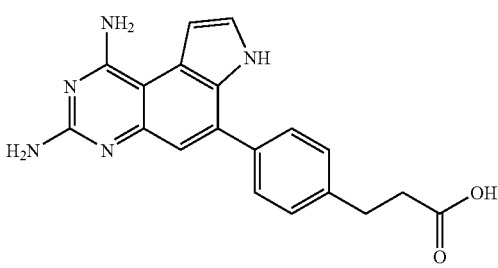

From 6-iodo-7H-pyrrolo[3,2-f]quinazoline-1,3-diamine and 3-[4-(4,4,5,5-Tetramethyl-[1,3,2]dioxaborolan-2-yl)-phenyl]-propionic acid there was produced 3-[4-(1,3-Diamino-7H-pyrrolo[3,2-f]quinazolin-6-yl)-phenyl]-propionic acid; LRMS for $C_{19}H_{17}N_5O_2$ $(M+H)^+$ at m/z=348.

Example 34

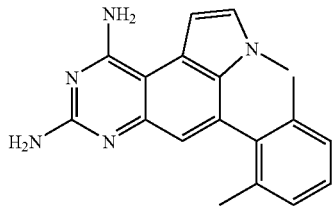

6(2,6Dimethyl-phenyl) 7-methyl-7H-pyrrolo[3,2-f]quinazoline-1,3diamine

A solution of 6-iodo-7-methyl-7H-pyrrolo[3,2-f]quinazoline-1,3-diamine (1.68 g, 5.00 mmol) in ethylene glycol dimethyl ether (10 mL) at 25° C. was treated with 2,6-dimethylbenzene boronic acid (1.50 g, 10.0 mmol) in ethanol (10 mL), sodium bicarbonate (2.84 g, 26.80 mmol), and tetrakis(triphenylphosphine)-palladium (0) (3.31 g, 2.86 mmol). The resulting mixture was heated to 80° C. for 3 h. The resulting mixture was filtered through a pad of celite and the filtrate diluted with water (100 mL). This solution was extracted with a 95/5/0.5 solution of methylene chloride/methanol/ammonium hydroxide (3×100 mL) and the combined organic layers dried over magnesium sulfate, filtered, and concentrated in vacuo. Flash chromatography (Merck Silica gel 60, 230-400 mesh, 90/5/0.5 methylene chloride/methanol/ammonium hydroxide) afforded 6-(2,6-dimethyl-phenyl)-7-methyl-7H-pyrrolo[3,2-f]quinazoline-1,3-diamine (100 mg, 6.34%) as an off-white solid; EI-HRMS m/e calcd for $C_{19}H_{19}N_5$ (M+) 317.1640. Found 317.1632.

In an analogous manner, there were obtained:

Example 35

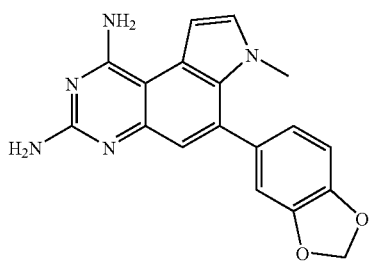

From 6-iodo-7-methyl-7H-pyrrolo[3,2-f]quinazoline-1,3-diamine and 3,4-methylenedioxyphenylboronic acid there was produced 6-Benzo[1,3]dioxol-5-yl-7-methyl-7H-pyrrolo[3,2-f]quinazoline-1,3-diamine trifluoro-acetic acid salt; LRMS for $C_{18}H_{15}N_5O_2$ (M+H)+ at m/z=334.

Example 36

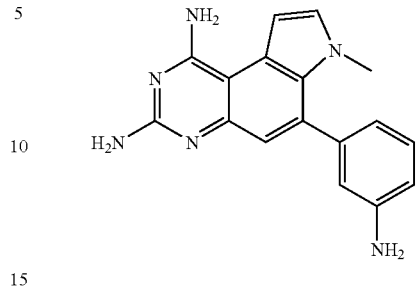

From 6-iodo-7-methyl-7H-pyrrolo[3,2-f]quinazoline-1,3-diamine and 3-aminobenzeneboronic acid there was produced 6-(3-Amino-phenyl)-7-methyl-7H-pyrrolo[3,2-f]quinazoline-1,3-diamine trifluoro-acetic acid salt as a white solid; LRMS for $C_{17}H_{16}N_6$ (M+H)+ at m/z=305.

Example 37

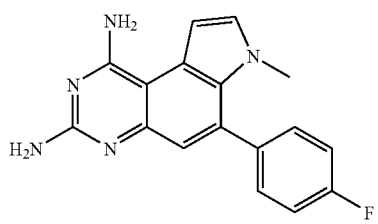

From 6-iodo-7-methyl-7H-pyrrolo[3,2-f]quinazoline-1,3-diamine and 4-fluorophenylboronic acid there was produced 6-(4-Fluoro-phenyl)-7-methyl-7H-pyrrolo[3,2-f]quinazoline-1,3-diamine trifluoro-acetic acid salt as a white solid; LRMS for $C_{17}H_{14}FN_5$ (M+H)+ at m/z=308.

Example 38

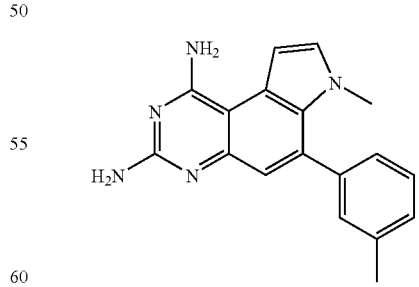

From 6-iodo-7-methyl-7H-pyrrolo[3,2-f]quinazoline-1,3-diamine and 3-methylphenylboronic acid there was produced 7-Methyl-6-m-tolyl-7H-pyrrolo[3,2-f]quinazoline-1,3-diamine trifluoro-acetic acid salt as a white solid; LRMS for $C_{18}H_{17}N_5$ (M+H)+ at m/z=304.

Example 39

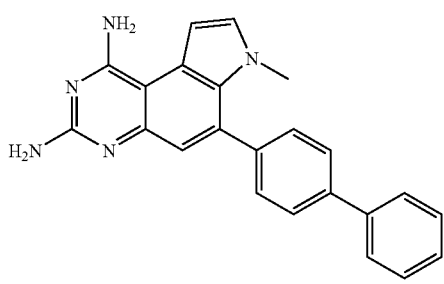

From 6-iodo-7-methyl-7H-pyrrolo[3,2-f]quinazoline-1,3-diamine and 4-biphenylboronic acid there was produced 6-Biphenyl-4-yl-7-methyl-7H-pyrrolo[3,2-f]quinazoline-1,3-diamine trifluoro-acetic acid salt as a white solid; LRMS for $C_{23}H_{19}N_5$ (M+H)$^+$ at m/z=366.

Example 40

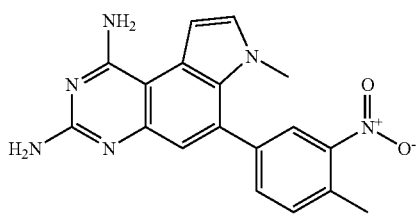

From 6-iodo-7-methyl-7H-pyrrolo[3,2-f]quinazoline-1,3-diamine and 4-methyl-3-nitrophenylboronic acid there was produced 7-methyl-6-(4-methyl-3-nitrophenyl)-7H-pyrrolo[3,2-f]quinazoline-1,3-diamine trifluoro-acetic acid salt as a white solid; LRMS for $C_{18}H_{16}N_6O_2$ (M+H)$^+$ for m/z=349.

Example 41

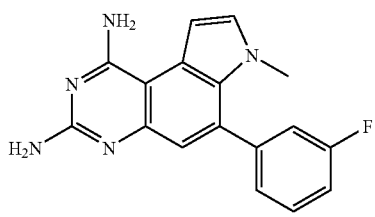

From 6-iodo-7-methyl-7H-pyrrolo[3,2-f]quinazoline-1,3-diamine and 3-fluorophenylboronic acid there was produced 6-(3-Fluoro-phenyl)-7-methyl-7H-pyrrolo[3,2-f]quinazoline-1,3-diamine trifluoro-acetic acid salt as a white solid; LRMS for $C_{17}H_{14}FN_5$ (M+H)$^+$ at m/z=308.

Example 42

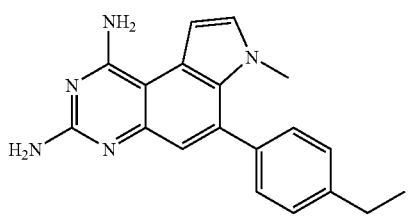

From 6-iodo-7-methyl-7H-pyrrolo[3,2-f]quinazoline-1,3-diamine and 4-ethylphenylboronic acid there was produced 6-(4-Ethyl-phenyl)-7-methyl-7H-pyrrolo[3,2-f]quinazoline-1,3-diamine trifluoro-acetic acid salt as a white solid; LRMS for $C_{19}H_{19}N_5$ (M+H)$^+$ at m/z=318.

Example 43

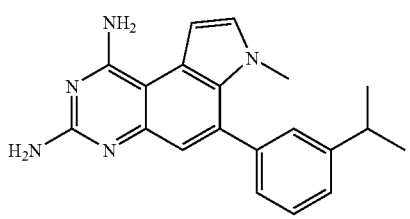

From 6-iodo-7-methyl-7H-pyrrolo[3,2-f]quinazoline-1,3-diamine and (3-isopropylphenyl)boronic acid there was produced 6-(3-Isopropyl-phenyl)-7-methyl-7H-pyrrolo[3,2-f]quinazoline-1,3-diamine trifluoro-acetic acid salt as a white solid; LRMS for $C_{20}H_{21}N_5$ (M+H)$^+$ at m/z=332.

Example 44

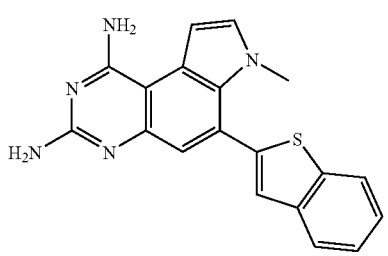

From 6-iodo-7-methyl-7H-pyrrolo[3,2-f]quinazoline-1,3-diamine and benzo[B]thiphene-2-boronic acid there was produced 6-Benzo[b]thiophen-2-yl-7-methyl-7H-pyrrolo[3,2-f]quinazoline-1,3-diamine trifluoro-acetic acid salt as a white solid; LRMS for $C_{19}H_{15}N_5S$ (M+H)$^+$ at m/z=346.

Example 45

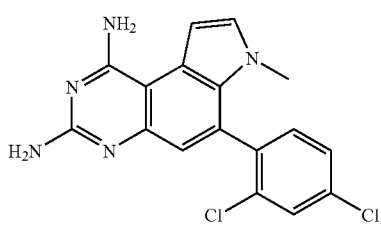

From 6-iodo-7-methyl-7H-pyrrolo[3,2-f]quinazoline-1,3-diamine and 2,4-dichlorophenylboronic acid there was produced 6-(2,4-Dichloro-phenyl)-7-methyl-7H-pyrrolo[3,2-f]quinazoline-1,3-diamine trifluoro-acetic acid salt as a white solid; LRMS for $C_{17}H_{13}Cl_2N_5$ (M+H)$^+$ at m/z=358.

Example 46

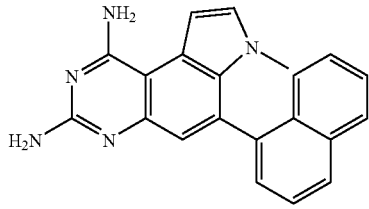

From 6-iodo-7-methyl-7H-pyrrolo[3,2-f]quinazoline-1,3diamine and 1-naphthaleneboronic acid there was produced 7-Methyl-6-naphthalen-1-yl-7H-pyrrolo[3,2-f]quinazoline-1,3-diamine trifluoro-acetic acid salt as a white solid; LRMS for $C_{21}H_{17}N_5$ (M+H)$^+$ at m/z=340.

Example 47

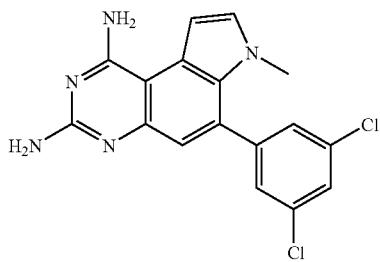

From 6-iodo-7-methyl-7H-pyrrolo[3,2-f]quinazoline-1,3-diamine and 3,5-dichlorophenylboronic acid there was produced 6-(3,5-Dichloro-phenyl)-7-methyl-7H-pyrrolo[3,2-f]quinazoline-1,3-diamine trifluoro-acetic acid salt as a white solid; LRMS for $C_{17}H_{13}Cl_2N_5$ (M+H)$^+$ at m/z=358.

Example 48

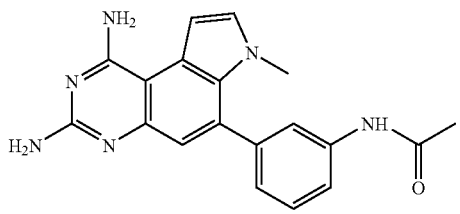

From 6-iodo-7-methyl-7H-pyrrolo[3,2-f]quinazoline-1,3-diamine and (3-acetylaminophenyl)boronic acid there was produced N-[3-(1,3-Diamino-7-methyl-7H-pyrrolo[3,2-f]quinazolin-6-yl)-phenyl]-acetamide trifluoro-acetic acid salt as a white solid; LRMS for $C_{19}H_{18}N_6O$ (M+H)$^+$ at m/z=347.

Example 49

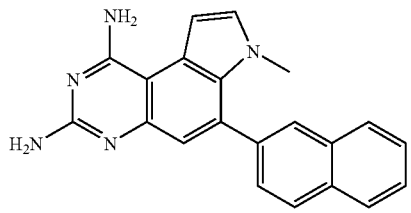

From 6-iodo-7-methyl-7H-pyrrolo[3,2-f]quinazoline-1,3-diamine and naphthalene-2-boronic acid there was produced 7-Methyl-6-naphthalen-2-yl-7H-pyrrolo[3,2-f]quinazoline-1,3-diamine trifluoro-acetic acid salt as a white solid; LRMS for $C_{21}H_{17}N_5$ (M+H)$^+$ at m/z=340.

Example 50

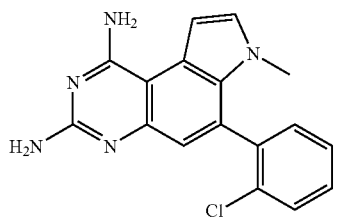

From 6-iodo-7-methyl-7H-pyrrolo[3,2-f]quinazoline-1,3-diamine and 2-chlorophenylboronic acid there was produced 6-(2-Chloro-phenyl)-7-methyl-7H-pyrrolo[3,2-f]quinazoline-1,3-diamine trifluoro-acetic acid salt as a white solid; LRMS for $C_{17}H_{14}ClN_5$ (M+H)$^+$ at m/z=324.

Example 51

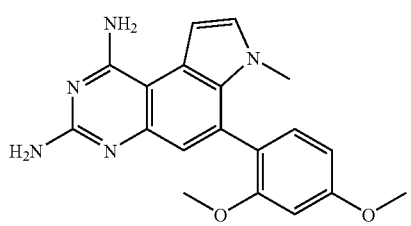

From 6-iodo-7-methyl-7H-pyrrolo[3,2-f]quinazoline-1,3-diamine and 2,4-dimethoxyphenylboronic acid there was produced 6-(2,4-Dimethoxy-phenyl)-7-methyl-7H-pyrrolo[3,2-f]quinazoline-1,3-diamine trifluoro-acetic acid salt as a white solid; LRMS for $C_{19}H_{19}N_5O_2$ (M+H)$^+$ at m/z=350.

Example 52

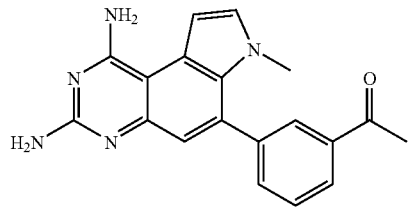

From 6-iodo-7-methyl-7H-pyrrolo[3,2-f]quinazoline-1,3-diamine and 3-acetylphenylboronic acid there was produced 1-[3-(1,3-Diamino-7-methyl-7H-pyrrolo[3,2-f]quinazolin-6-yl)-phenyl]-ethanone trifluoro-acetic acid salt as a white solid; LRMS for $C_{19}H_{17}N_5O$ $(M+H)^+$ at m/z=332.

Example 53

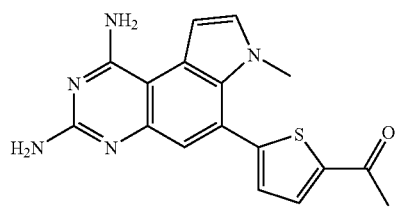

From 6-iodo-7-methyl-7H-pyrrolo[3,2-f]quinazoline-1,3-diamine and 5-acetyl-2-thiopheneboronic acid there was produced 1-[5-(1,3-Diamino-7-methyl-7H-pyrrolo[3,2-f]quinazolin-6-yl)-thiophen-2-yl]-ethanone trifluoro-acetic acid salt as a white solid; LRMS for $C_{17}H_{15}N_5OS$ $(M+H)^+$ at m/z=338.

Example 54

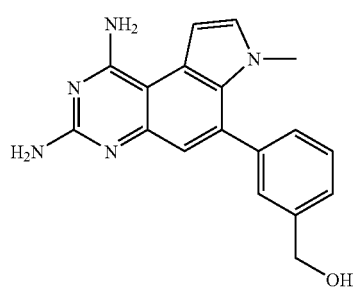

From 6-iodo-7-methyl-7H-pyrrolo[3,2-f]quinazoline-1,3-diamine and (3-hydroxymethylphenyl)boronic acid there was produced [3-(1,3-Diamino-7-methyl-7H-pyrrolo[3,2-f]quinazolin-6-yl)-phenyl]-methanol trifluoro-acetic acid salt; LRMS for $C_{18}H_{17}N_5O$ $(M+H)^+$ at m/z=320.

Example 55

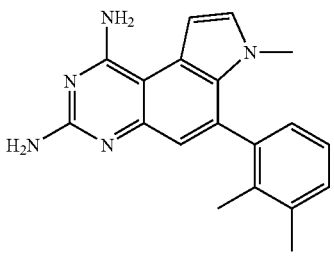

From 6-iodo-7-methyl-7H-pyrrolo[3,2-f]quinazoline-1,3-diamine and 2,3-dimethylphenylboronic acid there was produced 6-(2,3-Dimethyl-phenyl)-7-methyl-7H-pyrrolo[3,2-f]quinazoline-1,3-diamine trifluoro-acetic acid salt; LRMS for $C_{19}H_{19}N_5$ $(M+H)^+$ at m/z=318.

Example 56

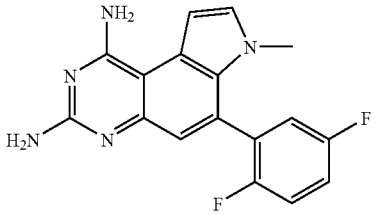

From 6-iodo-7-methyl-7H-pyrrolo[3,2-f]quinazoline-1,3-diamine and 2,5-difluorophenylboronic acid there was produced 6-(2,5-Difluoro-phenyl)-7-methyl-7H-pyrrolo[3,2-f]quinazoline-1,3-diamine trifluoro-acetic acid salt; LRMS for $C_{17}H_{13}F_2N_5$ $(M+H)^+$ at m/z=326.

Example 57

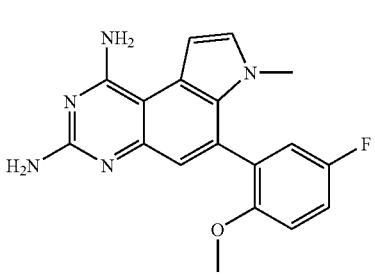

From 6-iodo-7-methyl-7H-pyrrolo[3,2-f]quinazoline-1,3-diamine and 5-fluoro-2-methoxyphenylboronic acid there was produced 6-(5-Fluoro-2-methoxy-phenyl)-7-methyl-7H-pyrrolo[3,2-f]quinazoline-1,3-diamine trifluoro-acetic acid salt; LRMS for $C_{18}H_{16}FN_5O$ $(M+H)^+$ at m/z=338.

Example 58

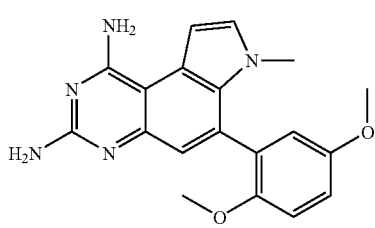

From 6-iodo-7-methyl-7H-pyrrolo[3,2-f]quinazoline-1,3-diamine and 2,5-dimethoxyphenylboronic acid there was produced 6-(2,5-Dimethoxy-phenyl)-7-methyl-7H-pyrrolo[3,2-f]quinazoline-1,3-diamine trifluoro-acetic acid salt; LRMS m/z calcd for $C_{19}H_{19}N_5O_2$ (M+H)$^+$ at m/z=350.

Example 59

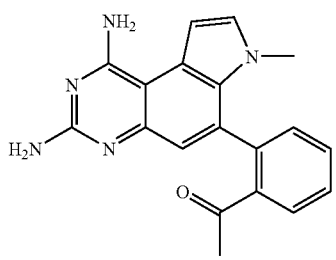

From 6-iodo-7-methyl-7H-pyrrolo[3,2-f]quinazoline-1,3-diamine and 2-acetylphenylboronic acid there was produced 1-[2-(1,3-Diamino-7-methyl-7H-pyrrolo[3,2-f]quinazolin-6-yl)-phenyl]-ethanone trifluoro-acetic acid salt; LRMS for $C_{19}H_{17}N_5O$ (M+H)$^+$ at m/z=332.

Example 60

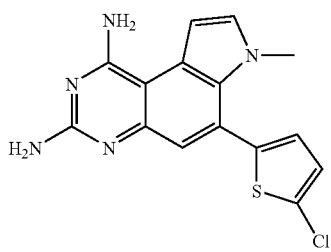

From 6-iodo-7-methyl-7H-pyrrolo[3,2-f]quinazoline-1,3-diamine and 5-chlorothiophene-2-boronic acid there was produced 6-(5-Chloro-thiophen-2-yl)-7-methyl-7H-pyrrolo[3,2-f]quinazoline-1,3-diamine trifluoro-acetic acid salt; LRMS for $C_{15}H_{12}ClN_5S$ (M+H)$^+$ at m/z=330.

Example 61

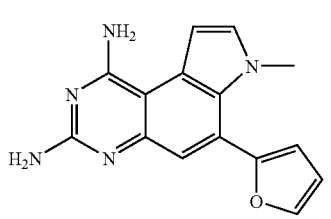

From 6-iodo-7-methyl-7H-pyrrolo[3,2-f]quinazoline-1,3-diamine and furan-2-boronic acid there was produced 6-Furan-2-yl-7-methyl-7H-pyrrolo[3,2-f]quinazoline-1,3-diamine trifluoro-acetic acid salt; LRMS for $C_{15}H_{13}N_5O$ (M+H)$^+$ at m/z=280.

Example 62

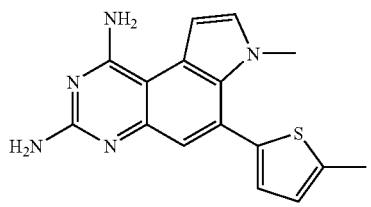

From 6-iodo-7-methyl-7H-pyrrolo[3,2-f]quinazoline-1,3-diamine and 5-methylthiophene-2-boronic acid there was produced 7-Methyl-6-(5-methyl-thiophen-2-yl)-7H-pyrrolo[3,2-f]quinazoline-1,3-diamine as an off-white solid; EI-HRMS m/e Calcd. for $C_{16}H_{15}N_5S$ (M+H)$^+$ 310.1121. Found 310.1125.

Example 63

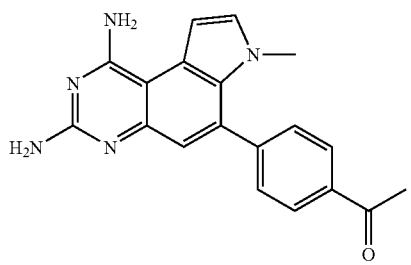

From 6-iodo-7-methyl-7H-pyrrolo[3,2-f]quinazoline-1,3-diamine and 4-acetylphenylboronic acid there was produced 1-[4-(1,3-Diamino-7-methyl-7H-pyrrolo[3,2-f]quinazolin-6-yl)-phenyl]-ethanone trifluoro-acetic acid salt; LRMS for $C_{19}H_{17}N_5O$ (M+H)$^+$ at m/z=332.

Example 64

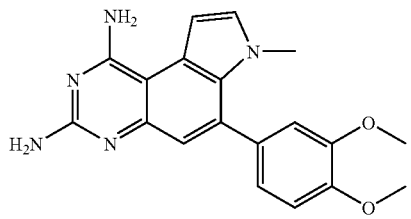

From 6-iodo-7-methyl-7H-pyrrolo[3,2-f]quinazoline-1,3-diamine and 3,4-dimethoxyphenylboronic acid there was produced 6-(3,4-Dimethoxy-phenyl)-7-methyl-7H-pyrrolo[3,2-f]quinazoline-1,3-diamine trifluoro-acetic acid salt; LRMS for $C_{19}H_{19}N_5O_2$ (M+H)$^+$ at m/z=350.

Example 65

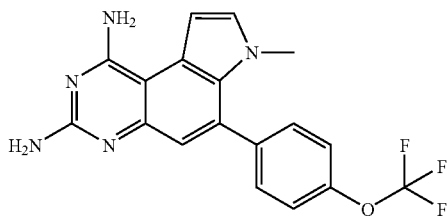

From 6-iodo-7-methyl-7H-pyrrolo[3,2-f]quinazoline-1,3-diamine and 4-(trifluoromethoxy)benzeneboronic acid there was produced 7-Methyl-6-(4-trifluoromethoxy-phenyl)-7H-pyrrolo[3,2-f]quinazoline-1,3-diamine trifluoro-acetic acid salt; LRMS for $C_{18}H_{14}F_3N_5O$ (M+H)$^+$ at m/z=374.

Example 66

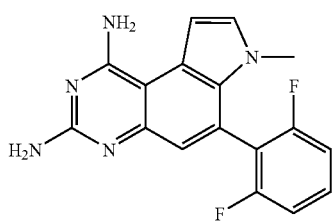

From 6-iodo-7-methyl-7H-pyrrolo[3,2-f]quinazoline-1,3-diamine and 2,6-difluorophenylboronic acid there was produced 6-(2,6-Difluoro-phenyl)-7-methyl-7H-pyrrolo[3,2-f]quinazoline-1,3-diamine trifluoro-acetic acid salt; LRMS for $C_{17}H_{13}F_2N_5$ (M+H)$^+$ at m/z=326.

Example 67

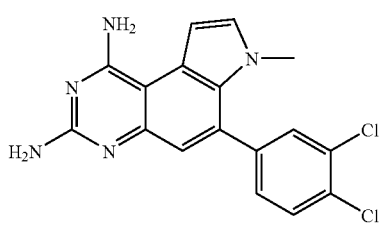

From 6-iodo-7-methyl-7H-pyrrolo[3,2-f]quinazoline-1,3-diamine and 3,4-dichlorophenylboronic acid there was produced 6-(3,4-Dichloro-phenyl)-7-methyl-7H-pyrrolo[3,2-f]quinazoline-1,3-diamine trifluoro-acetic acid salt; LRMS for $C_{17}H_{13}Cl_2N_5$ (M+H)$^+$ at m/z=358.

Example 68

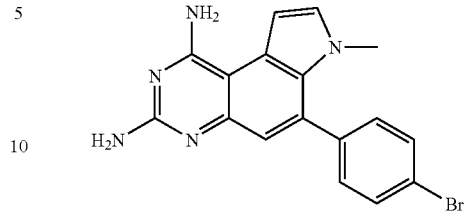

From 6-iodo-7-methyl-7H-pyrrolo[3,2-f]quinazoline-1,3-diamine and 4-bromophenylboronic acid there was produced 6-(4-Bromo-phenyl)-7-methyl-7H-pyrrolo[3,2-f]quinazoline-1,3-diamine trifluoro-acetic acid salt; LRMS for $C_{17}H_{14}BrN_5$ (M+H)$^+$ at m/z=368.

Example 69

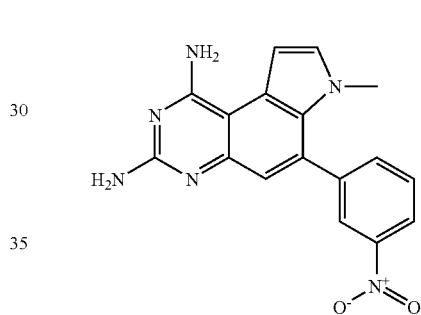

From 6-iodo-7-methyl-7H-pyrrolo[3,2-f]quinazoline-1,3-diamine and 3-nitrophenylboronic acid there was produced 7-methyl-6-(3-nitro-phenyl)-7H-pyrrolo[3,2-f]quinazoline-1,3-diamine trifluoro-acetic acid salt; LRMS for $C_{17}H_{14}N_6O_2$ (M+H)$^+$ at m/z=335.

Example 70

From 6-iodo-7-methyl-7H-pyrrolo[3,2-f]quinazoline-1,3-diamine and 4-(ethylthio)phenylboronic acid there was produced 6-(4-Ethylsulfanyl-phenyl)-7-methyl-7H-pyrrolo[3,2-f]quinazoline-1,3-diamine trifluoro-acetic acid salt; LRMS for $C_{19}H_{19}N_5S$ (M+H)$^+$ at m/z=350.

Example 71

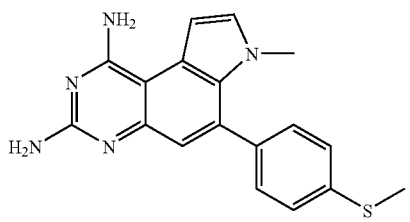

From 6-iodo-7-methyl-7H-pyrrolo[3,2-f]quinazoline-1,3-diamine and 4-(methylthio)phenylboronic acid there was produced 7-Methyl-6-(4-methylsulfanyl-phenyl)-7H-pyrrolo[3,2-f]quinazoline-1,3-diamine trifluoro-acetic acid salt; LRMS for $C_{18}H_{17}N_5S$ (M+H)$^+$ at m/z=336.

Example 72

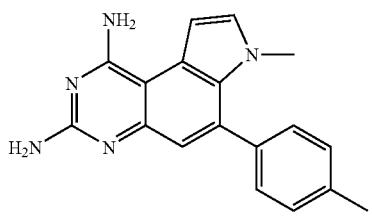

From 6-iodo-7-methyl-7H-pyrrolo[3,2-f]quinazoline-1,3-diamine and 4-methylphenylboronic acid there was produced 7-Methyl-6-p-tolyl-7H-pyrrolo[3,2-f]quinazoline-1,3-diamine trifluoro-acetic acid salt; LRMS for $C_{18}H_{17}N_5$ (M+H)$^+$ at m/z=304.

Example 73

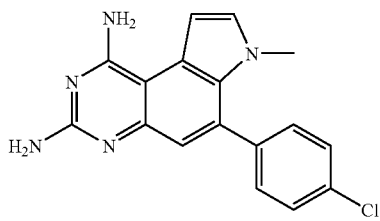

From 6-iodo-7-methyl-7H-pyrrolo[3,2-f]quinazoline-1,3-diamine and 4-chlorophenylboronic acid there was produced 6-(4-Chloro-phenyl)-7-methyl-7H-pyrrolo[3,2-f]quinazoline-1,3-diamine trifluoro-acetic acid salt; LRMS for $C_{17}H_{14}ClN_5$ (M+H)$^+$ at m/z=324.

Example 74

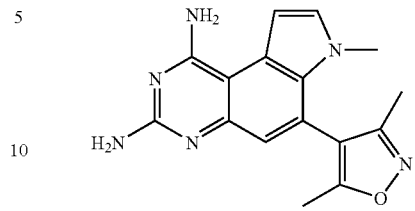

From 6-iodo-7-methyl-7H-pyrrolo[3,2-f]quinazoline-1,3-diamine and 3,5-dimethylisoxazole-4-boronic acid there was produced 6-(3,5-Dimethyl-isoxazol-4-yl)-7-methyl-7H-pyrrolo[3,2-f]quinazoline-1,3-diamine trifluoro-acetic acid salt; LRMS for $C_{16}H_{16}N_6O$ (M+H)$^+$ at m/z=309.

Example 75

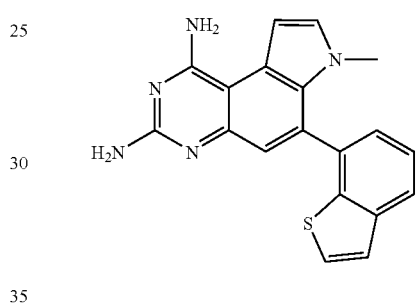

From 6-iodo-7-methyl-7H-pyrrolo[3,2-f]quinazoline-1,3-diamine and benzothiophene-7-boronic acid there was produced 6-(3,5-6-Benzo[b]thiophen-7-yl-7-methyl-7H-pyrrolo[3,2-f]quinazoline-1,3-diamine trifluoro-acetic acid salt; LRMS for $C_{19}H_{15}N_5S$ (M+H)$^+$ at m/z=346.

Example 76

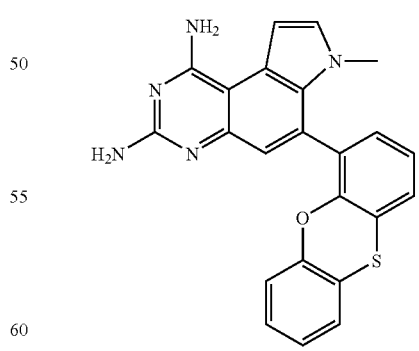

From 6-iodo-7-methyl-7H-pyrrolo[3,2-f]quinazoline-1,3-diamine and phenoxathin-4-boronic acid there was produced 7-Methyl-6-phenoxathiin-4-yl-7H-pyrrolo[3,2-f]quinazoline-1,3-diamine trifluoro-acetic acid salt; LRMS for $C_{23}H_{17}N_5OS$ (M+H)$^+$ at m/z=412.

Example 77

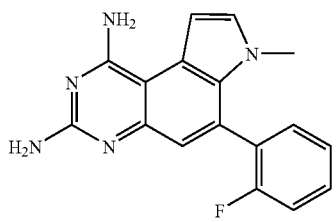

From 6-iodo-7-methyl-7H-pyrrolo[3,2-f]quinazoline-1,3-diamine and 2-fluorophenylboronic acid there was produced 6-(2-Fluoro-phenyl)-7-methyl-7H-pyrrolo[3,2-f]quinazoline-1,3-diamine trifluoro-acetic acid salt; LRMS for $C_{17}H_{14}FN_5$ (M+H)$^+$ at m/z=308.

Example 78

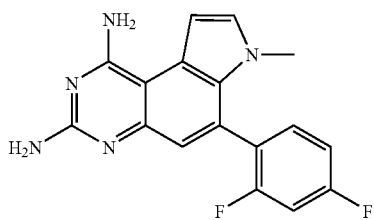

From 6-iodo-7-methyl-7H-pyrrolo[3,2-f]quinazoline-1,3-diamine and 2,4-difluorobenzeneboronic acid there was produced 6-(2,4-Difluoro-phenyl)-7-methyl-7H-pyrrolo[3,2-f]quinazoline-1,3-diamine trifluoro-acetic acid salt; LRMS for $C_{17}H_{13}F_2N_5$ (M+H)$^+$ at m/z=326.

Example 79

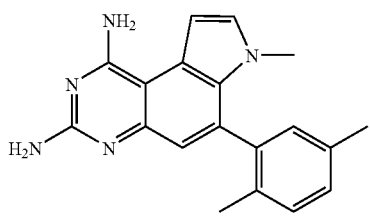

From 6-iodo-7-methyl-7H-pyrrolo[3,2-f]quinazoline-1,3-diamine and 2,5-dimethylphenylboronic acid there was produced 6-(2,5-Dimethyl-phenyl)-7-methyl-7H-pyrrolo[3,2-f]quinazoline-1,3-diamine trifluoro-acetic acid salt; LRMS for $C_{19}H_{19}N_5$ (M+H)$^+$ at m/z=318.

Example 80

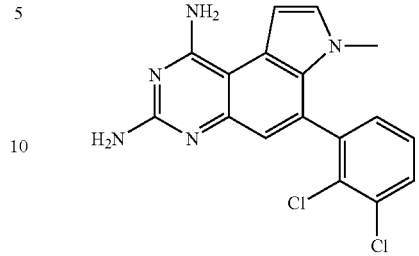

From 6-iodo-7-methyl-7H-pyrrolo[3,2-f]quinazoline-1,3-diamine and 2,3-dichlorophenylboronic acid there was produced 6-(2,3-Dichloro-phenyl)-7-methyl-7H-pyrrolo[3,2-f]quinazoline-1,3-diamine trifluoro-acetic acid salt; LRMS for $C_{17}H_{13}Cl_2N_5$ (M+H)$^+$ at m/z=358.

Example 81

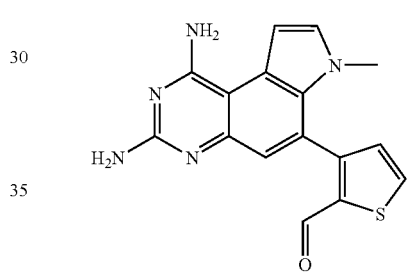

From 6-iodo-7-methyl-7H-pyrrolo[3,2-f]quinazoline-1,3-diamine and 2-formyl-3-thiopheneboronic acid there was produced 3-(1,3-Diamino-7-methyl-7H-pyrrolo[3,2-f]quinazolin-6-yl)-thiophene-2-carbaldehyde trifluoro-acetic acid salt; LRMS for $C_{16}H_{13}N_5OS$ (M+H)$^+$ at m/z=324.

Example 82

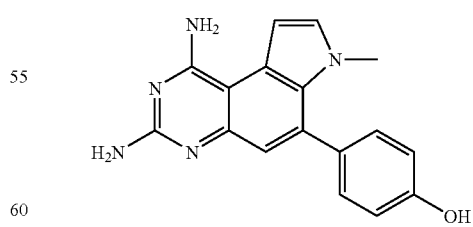

From 6-iodo-7-methyl-7H-pyrrolo[3,2-f]quinazoline-1,3-diamine and (4-hydroxyphenyl)boronic acid there was produced 4-(1,3-Diamino-7-methyl-7H-pyrrolo[3,2-f]quinazolin-6-yl)-phenol trifluoro-acetic acid salt; LRMS for $C_{17}H_{15}N_5O$ (M+H)$^+$ at m/z=306.

Example 83

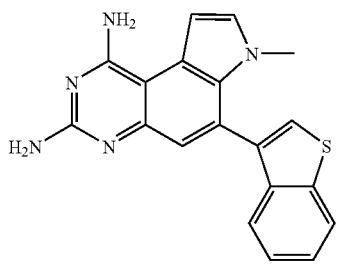

From 6-iodo-7-methyl-7H-pyrrolo[3,2-f]quinazoline-1,3-diamine and 1-benzothiophen-3-ylboronic acid there was produced 6-Benzo[b]thiophen-3-yl-7-methyl-7H-pyrrolo[3,2-f]quinazoline-1,3-diamine trifluoro-acetic acid salt; LRMS for $C_{19}H_{15}N_5S$ (M)$^+$ at m/z=345.

Example 84

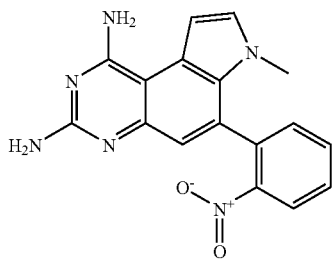

From 6-iodo-7-methyl-7H-pyrrolo[3,2-f]quinazoline-1,3-diamine and (2-nitrophenyl)boronic acid there was produced 7-methyl-6-(2-nitro-phenyl)-7H-pyrrolo[3,2-f]quinazoline-1,3-diamine trifluoro-acetic acid salt; LRMS for $C_{17}H_{14}N_6O_2$ (M+H)$^+$ at m/z=335.

Example 85

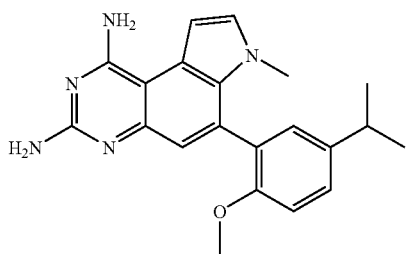

From 6-iodo-7-methyl-7H-pyrrolo[3,2-f]quinazoline-1,3-diamine and 5-isopropyl-2-methoxybenzeneboronic acid there was produced 6-(5-Isopropyl-2-methoxy-phenyl)-7-methyl-7H-pyrrolo[3,2-f]quinazoline-1,3-diamine trifluoro-acetic acid salt; LRMS for $C_{21}H_{23}N_5O$ (M+H)$^+$ at m/z=362.

Example 86

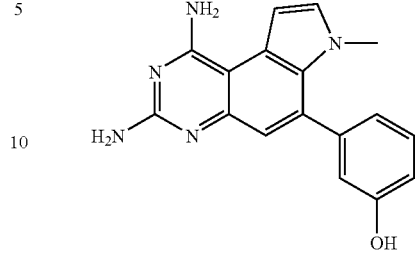

From 6-iodo-7-methyl-7H-pyrrolo[3,2-f]quinazoline-1,3-diamine and (3-hydroxyphenyl)boronic acid there was produced 3-(1,3-Diamino-7-methyl-7H-pyrrolo[3,2-f]quinazolin-6-yl)-phenol trifluoro-acetic acid salt; LRMS for $C_{17}H_{15}N_5O$ (M+H)$^+$ at m/z=306.

Example 87

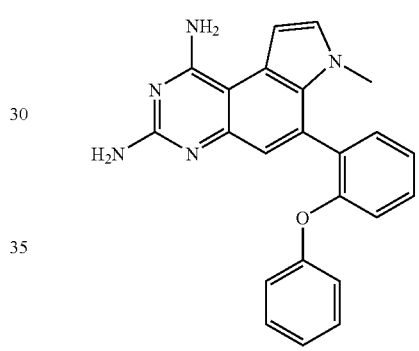

From 6-iodo-7-methyl-7H-pyrrolo[3,2-f]quinazoline-1,3-diamine and 2-(phenoxy)phenylboronic acid there was produced 7-Methyl-6-(2-phenoxy-phenyl)-7H-pyrrolo[3,2-f]quinazoline-1,3-diamine trifluoro-acetic acid salt; LRMS for $C_{23}H_{19}N_5O$ (M+H)$^+$ at m/z=382.

Example 88

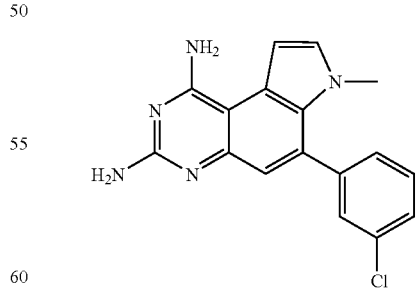

From 6-iodo-7-methyl-7H-pyrrolo[3,2-f]quinazoline-1,3-diamine and 3-chlorophenylboronic acid there was produced 6-(3-Chloro-phenyl)-7-methyl-7H-pyrrolo[3,2-f]quinazoline-1,3-diamine trifluoro-acetic acid salt; LRMS for $C_{17}H_{14}ClN_5$ (M+H)$^+$ at m/z=324.

Example 89

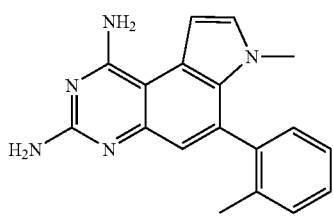

From 6-iodo-7-methyl-7H-pyrrolo[3,2-f]quinazoline-1,3-diamine and o-tolylboronic acid there was produced 7-Methyl-6-o-tolyl-7H-pyrrolo[3,2-f]quinazoline-1,3-diamine trifluoro-acetic acid salt; LRMS for $C_{18}H_{17}N_5$ (M+H)$^+$ at m/z=304.

Example 90

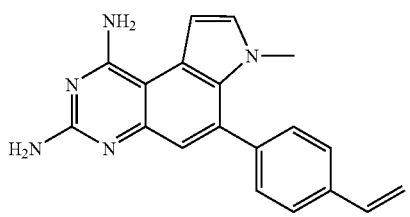

From 6-iodo-7-methyl-7H-pyrrolo[3,2-f]quinazoline-1,3-diamine and 4-vinylphenylboronic acid there was produced 7-Methyl-6-(4-vinyl-phenyl)-7H-pyrrolo[3,2-f]quinazoline-1,3-diamine trifluoro-acetic acid salt; LRMS for $C_{19}H_{17}N_5$ (M+H)$^+$ at m/z=316.

Example 91

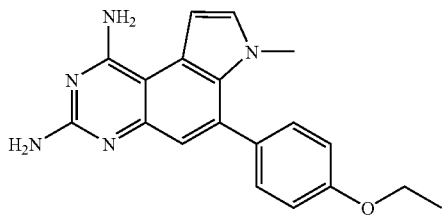

From 6-iodo-7-methyl-7H-pyrrolo[3,2-f]quinazoline-1,3-diamine and 4-ethoxyphenylboronic acid there was produced 6-(4-Ethoxy-phenyl)-7-methyl-7H-pyrrolo[3,2-f]quinazoline-1,3-diamine trifluoro-acetic acid salt; LRMS for $C_{19}H_{19}N_5O$ (M+H)$^+$ at m/z=334.

Example 92

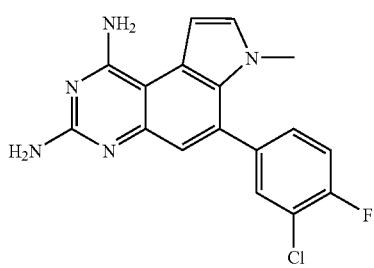

From 6-iodo-7-methyl-7H-pyrrolo[3,2-f]quinazoline-1,3-diamine and 3-chloro-4-fluorophenylboronic acid there was produced 6-(3-Chloro-4-fluoro-phenyl)-7-methyl-7H-pyrrolo[3,2-f]quinazoline-1,3-diamine trifluoro-acetic acid salt; LRMS for $C_{17}H_{13}ClFN_5$ (M+H)$^+$ at m/z=342.

Example 93

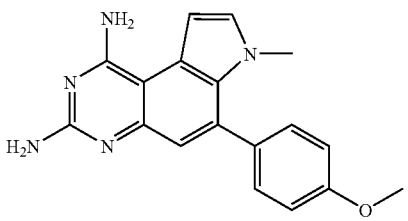

From 6-iodo-7-methyl-7H-pyrrolo[3,2-f]quinazoline-1,3-diamine and 4-methoxyphenylboronic acid there was produced 6-(4-Methoxy-phenyl)-7-methyl-7H-pyrrolo[3,2-f]quinazoline-1,3-diamine trifluoro-acetic acid salt; LRMS for $C_{18}H_{17}N_5O$ (M+H)$^+$ at m/z=320.

Example 94

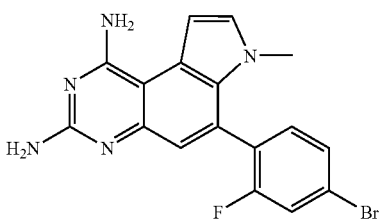

From 6-iodo-7-methyl-7H-pyrrolo[3,2-f]quinazoline-1,3-diamine and 4-bromo-2-fluorobenzeneboronic acid there was produced 6-(4-Bromo-2-fluoro-phenyl)-7-methyl-7H-pyrrolo[3,2-f]quinazoline-1,3-diamine trifluoro-acetic acid salt; LRMS for $C_{17}H_{13}BrFN_5$ (M+H)$^+$ at m/z=386.

Example 95

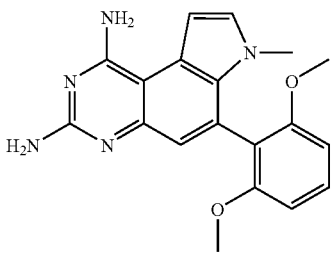

From 6-iodo-7-methyl-7H-pyrrolo[3,2-f]quinazoline-1,3-diamine and 2,6-dimethoxyphenylboronic acid there was produced 6-(2,6-Dimethoxy-phenyl)-7-methyl-7H-pyrrolo[3,2-f]quinazoline-1,3-diamine trifluoro-acetic acid salt; LRMS for $C_{19}H_{19}N_5O_2$ (M+H)$^+$ at m/z=350.

Example 96

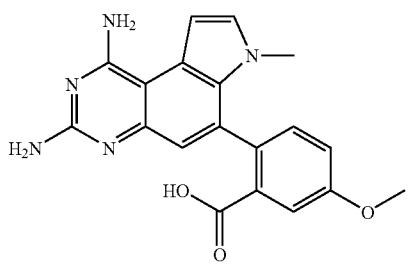

From 6-iodo-7-methyl-7H-pyrrolo[3,2-f]quinazoline-1,3-diamine and 2-tert-butoxycarbonyl-4-methoxyphenylboronic acid there was produced 2-(1,3-Diamino-7-methyl-7H-pyrrolo[3,2-f]quinazolin-6-yl)-5-methoxy-benzoic acid trifluoro-acetic acid salt; LRMS for $C_{19}H_{17}N_5O_3$ (M+H)$^+$ at m/z=364.

Example 97

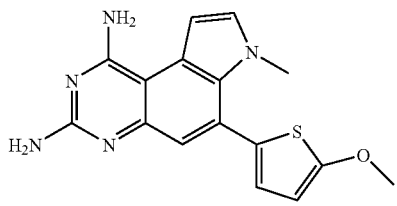

From 6-iodo-7-methyl-7H-pyrrolo[3,2-f]quinazoline-1,3-diamine and 5-methoxy thiopheneboronic acid there was produced 6-(5-Methoxy-thiophen-2-yl)-7-methyl-7H-pyrrolo[3,2-f]quinazoline-1,3-diamine as a light yellow solid; EI-HRMS m/e Calcd for $C_{16}H_{15}N_5OS$ (M$^+$) 325.0997. Found 325.0994.

Example 98

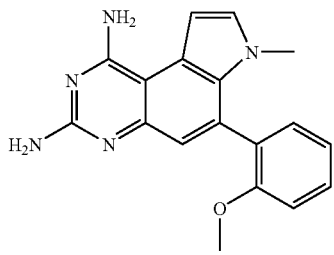

From 6-iodo-7-methyl-7H-pyrrolo[3,2-f]quinazoline-1,3-diamine and 2-methoxyphenylboronic acid there was produced 6-(2-Methoxy-phenyl)-7-methyl-7H-pyrrolo[3,2-f]quinazoline-1,3-diamine as a light brown solid; LRMS for $C_{18}H_{17}N_5O$ (M+H)$^+$ at m/z=320.

Example 99

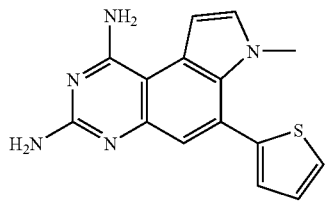

From 6-iodo-7-methyl-7H-pyrrolo[3,2-f]quinazoline-1,3-diamine and thiophene-2-boronic acid there was produced 7-Methyl-6-thiophen-2-yl-7H-pyrrolo[3,2-f]quinazoline-1,3-diamine as a light yellow solid; LRMS for $C_{15}H_{13}N_5S$ (M+Na)$^+$ at m/z=318.

Example 100

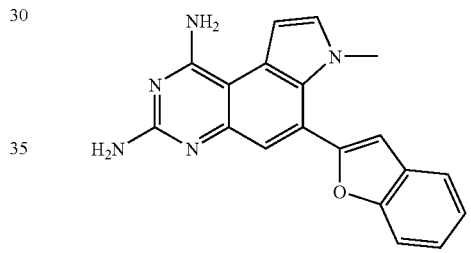

From 6-iodo-7-methyl-7H-pyrrolo[3,2-f]quinazoline-1,3-diamine and benzo[B]furan-2-boronic acid there was produced 6-Benzofuran-2-yl-7-methyl-7H-pyrrolo[3,2-f]quinazoline-1,3-diamine as a yellow solid; LRMS for $C_{19}H_{15}N_5O$ (M+H)$^+$ at m/z=330.

Example 101

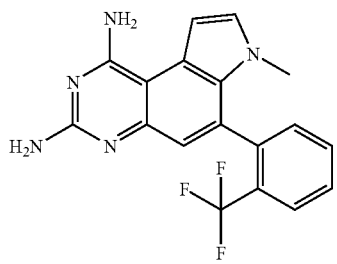

From 6-iodo-7-methyl-7H-pyrrolo[3,2-f]quinazoline-1,3-diamine and 2-(trifluoromethyl)benzeneboronic acid there was produced 7-Methyl-6-(2-trifluoromethyl-phenyl)-7H-pyrrolo[3,2-f]quinazoline-1,3-diamine as a yellow solid; LRMS for $C_{18}H_{14}F_3N_5$ (M+H)$^+$ at m/z=358.

Example 102

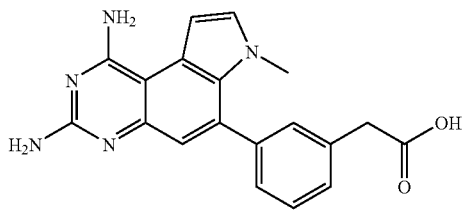

From 6-iodo-7-methyl-7H-pyrrolo[3,2-f]quinazoline-1,3-diamine and [3-(4,4,5,5-Tetramethyl-[1,3,2]dioxaborolan-2-yl)-phenyl]-acetic acid there was produced [3-(1,3-Diamino-7-methyl-7H-pyrrolo[3,2-f]quinazolin-6-yl)-phenyl]-acetic acid; LRMS for $C_{19}H_{17}N_5O_2$ (M+H)$^+$ at m/z=348.

Example 103

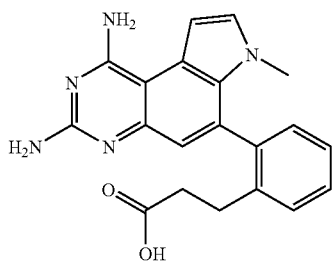

From 6-iodo-7-methyl-7H-pyrrolo[3,2-f]quinazoline-1,3-diamine and 3-[2-(4,4,5,5-Tetramethyl-[1,3,2]dioxaborolan-2-yl)-phenyl]-propionic acid there was produced 3-[2-(1,3-Diamino-7-methyl-7H-pyrrolo[3,2-f]quinazolin-6-yl)-phenyl]-propionic acid; LRMS for $C_{20}H_{19}N_5O_2$ (M+H)$^+$ at m/z=362.

Example 104

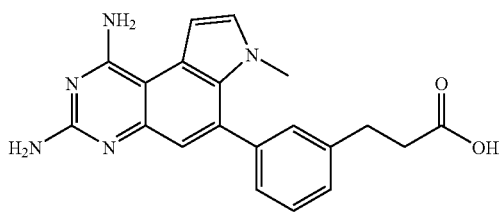

From 6-iodo-7-methyl-7H-pyrrolo[3,2-f]quinazoline-1,3-diamine and 3-[3-(4,4,5,5-Tetramethyl-[1,3,2]dioxaborolan-2-yl)-phenyl]-propionic acid there was produced 3-[3-(1,3-Diamino-7-methyl-7H-pyrrolo[3,2-f]quinazolin-6-yl)-phenyl]-propionic acid; LRMS for $C_{20}H_{19}N_5O_2$ (M+H)$^+$ at m/z=362.

Example 105

7-Methanesulfonyl-6-thiophen-2-yl-7H-pyrrolo[3,2-f]quinazoline-1,3-diamine trifluoro-acetic acid salt

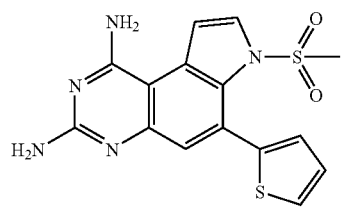

To a slurry of 6-Thiophen-2-yl-7H-pyrrolo[3,2-f]quinazoline-1,3-diamine (example 100), prepared as described in example 1 from 6-iodo-7H-pyrrolo[3,2-f]quinazoline-1,3-diamine VI and 2-thiopheneboronic acid, (50 mg, 0.178 mmole) in anhydrous DMF (3 ml) at room temperature was added sodium hydride (60% in mineral oil, 8 mg, 0.20 mmole) and the mixture was stirred at room temperature for 45 minutes. The above mixture was cooled in an ice bath, methanesulfonyl chloride was slowly added dropwise (0.016 ml, 0.207 mmole) and stirred at 0° C. for 30 minutes. The mixture was then warmed up to room temperature and stirred overnight. Additional amounts of sodium hydride (8 mg) and methanesulfonyl chloride (0.016 ml) was added the next day to drive the reaction to completion and the mixture was stirred at room temperature for an additional 20 hours. The mixture was evaporated to dryness and the crude mixture was purified by reversed phase HPLC to give 7-Methanesulfonyl-6-thiophen-2-yl-7H-pyrrolo[3,2-f]quinazoline-1,3-diamine trifluoro-acetic acid salt as a light brown solid; LRMS m/z calcd for $C_{15}H_{13}N_5O_2S_2$ (M+H)$^+$ at m/z=360.

Example 106

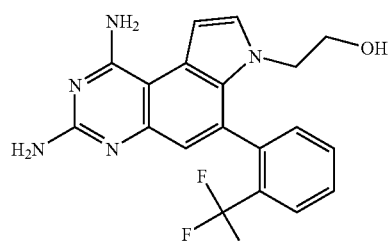

From 2-(1,3-Diamino-6-iodo-pyrrolo[3,2-f]quinazolin-7-yl)-ethanol and 2-(trifluoromethyl)benzeneboronic acid there was produced 2-[1,3-Diamino-6-(2-trifluoromethyl-phenyl)-pyrrolo[3,2-f]quinazolin-7-yl]-ethanol trifluoro-acetic acid salt as an off-white solid; LRMS for $C_{19}H_{16}F_3N_5O$ (M+H)$^+$ at m/z=388.

Example 107

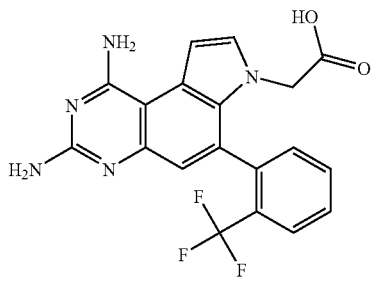

From (1,3-Diamino-6-iodo-pyrrolo[3,2-f]quinazolin-7-yl)-acetic acid and 2-(trifluoromethyl)benzeneboronic acid there was produced [1,3-Diamino-6-(2-trifluoromethyl-phenyl)-pyrrolo[3,2-f]quinazolin-7-yl]-acetic acid trifluoro-acetic acid salt as an off-white solid; LRMS for $C_{19}H_{14}F_3N_5O_2$ (M+H)$^+$ at m/z=402.

Example 108

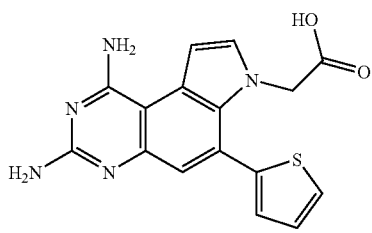

From (1,3-Diamino-6-iodo-pyrrolo[3,2-f]quinazolin-7-yl)-acetic acid and thiophene-2-boronic acid there was produced (1,3-Diamino-6-thiophen-2-yl-pyrrolo[3,2-f]quinazolin-7-yl)-acetic acid trifluoro-acetic acid salt as an off-white solid; LRMS for $C_{16}H_{13}N_5O_2S$ (M+H)$^+$ at m/z=340.

Example 109

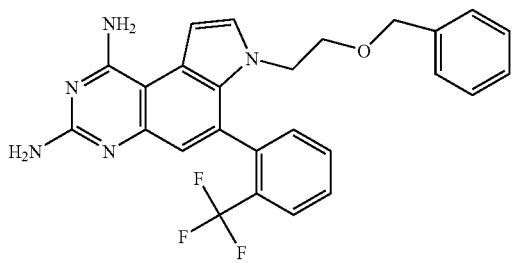

From 7-(2-Benzyloxy-ethyl)-6-iodo-7H-pyrrolo[3,2-f]quinazoline-1,3-diamine and 2-(trifluoromethyl)benzeneboronic acid there was produced 7-(2-Benzyloxy-ethyl)-6-(2-trifluoromethyl-phenyl)-7H-pyrrolo[3,2-f]quinazoline-1,3-diamine trifluoro-acetic acid salt as a light brown solid; LRMS for $C_{26}H_{22}F_3N_5O$ (M+H)$^+$ at m/z=478.

Example 110

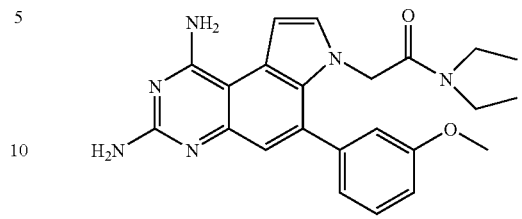

From 2-(1,3-Diamino-6-iodo-pyrrolo[3,2-f]quinazolin-7-yl)—N,N-diethyl-acetamide and 3-methoxyphenylboronic acid there was produced 2-[1,3-Diamino-6-(3-methoxy-phenyl)-pyrrolo[3,2-f]quinazolin-7-yl]-N,N-diethyl-acetamide as a yellow solid; LRMS for $C_{23}H_{26}N_6O_2$ (M+H)$^+$ at m/z=419.

Example 111

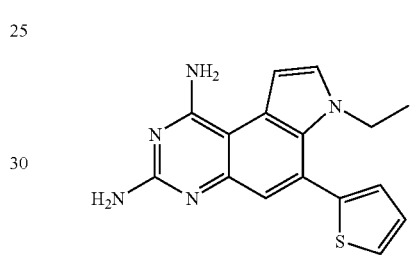

From 7-Ethyl-6-iodo-7H-pyrrolo[3,2-f]quinazoline-1,3-diamine and thiophene-2-boronic acid there was produced 7-Ethyl-6-thiophen-2-yl-7H-pyrrolo[3,2-f]quinazoline-1,3-diamine as an off-white solid; $^1$H NMR (DMSO-d$_6$, 300 MHz) δ 7.69 (d, J=5.13 Hz, 1H), 7.49 (d, J=2.56 Hz, 1H), 7.27 (m, 1H), 7.18 (m, 1H), 7.14 (d, J=2.56 Hz, 1H), 6.91 (s, 1H), 6.81 (broad s, 2H), 5.82 (broad S, 2H), 3.82 (q, J=6.96 Hz, 2H), 0.99 (t, J=6.96 Hz, 3H).

Example 112

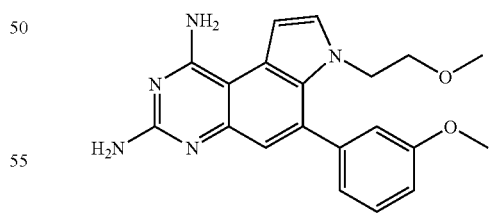

From 6-Iodo-7-(2-methoxy-ethyl)-7H-pyrrolo[3,2-f]quinazoline-1,3-diamine and 3-methoxyphenylboronic acid there was produced 7-(2-Methoxy-ethyl)-6-(3-methoxy-phenyl)-7H-pyrrolo[3,2-f]quinazoline-1,3-diamine as a light-brown solid; LRMS for $C_{20}H_{21}N_5O_2$ (M+H)$^+$ at m/z=364.

Scheme 5 is directed to the synthesis of 8 methyl derivatives.

SCHEME 5

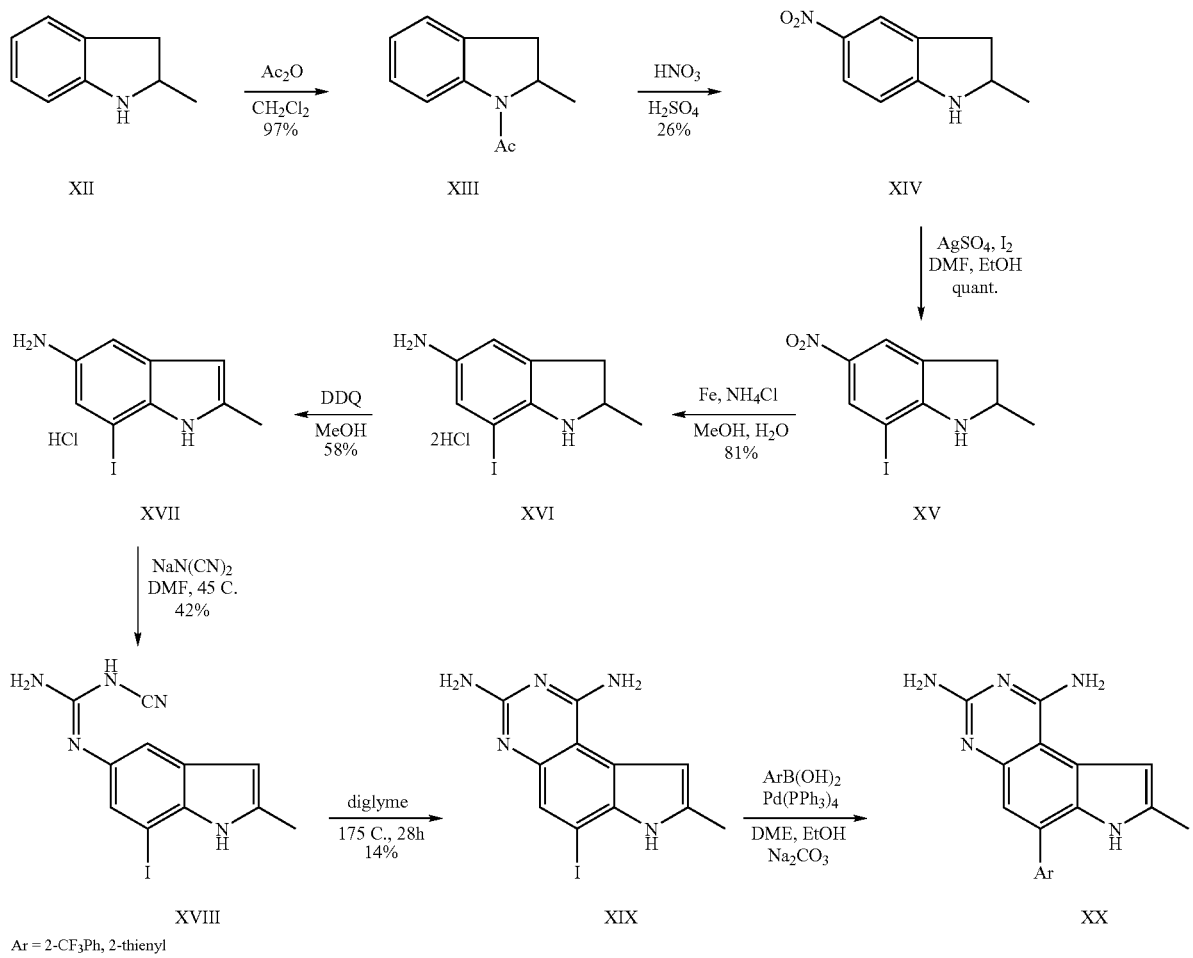

Ar = 2-CF₃Ph, 2-thienyl

Example 113

8-Methyl-6-thiophen-2-yl-7H-pyrrolo[3,2-f]quinazoline-1,3-diamine trifluoroacetic acid salt

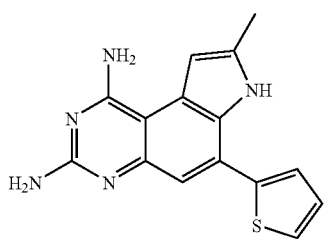

To a cooled (0-10 C.) mixture of concentrated nitric acid (12 mL) and concentrated sulfuric acid (40 mL) was added 1-acetyl-2-methyl-indoline XII (12.5 g, 0.0713 moles), prepared by an analgous method to that described in Chem.Ber.; 14; 1881; 890, in small portions so that the internal temperature of the reaction remained between 10-20° C. The resulting mixture was allowed to stir at 5-10° C. overnight. The mixture was poured slowly into 300 mL of cold water and the precipitate that formed was collected by filtration, washed with water and redissolved in an ethanol-6N HCl solution and warmed to reflux for 30 minutes. The resulting solution was concentrated, EtOAc was added and the Ph of the solution adjusted to 10. The organic phase was separated and dried over MgSO$_4$. The mixture was filtered, and evaporated and the crude material purified by column chromatography (50% EtOAc-Hexane) to give 3.31 g, 26% of 2-methyl-5-nitro-2,3-dihydro-1H-indole XIII: LRMS for $C_9H_{10}N_2O_2$ (M+H)$^+$ at m/z=179.

A mixture of silver sulfate (4.92 g, 0.0157 mol) and iodine (4 g, 0.0.0157 mol) in N,N-dimethylformamide (50 mL) and ethanol (100 mL) was treated with 2-methyl-5-nitro-2,3-dihydro-1H-indole XIII (3.31 g, 0.015 mol) and the resulting mixture was stirred at 25° C. for 30 min before an additional 1 g of iodine was added and the stirring continued for 2 h. The resulting reaction mixture was filtered and the solids washed with ethyl acetate before being concentrated in vacuo to a volume of approximately 50 mL. This solution was treated with a 1.0N aqueous sodium thiosulfate solution (100 mL) and a saturated aqueous sodium chloride solution (200 mL). The resulting precipitate was collected by filtration, washed with water and petroleum ether, and dried in vacuo to 7-iodo-2-methyl-5-nitro-2,3-dihydro-1H-indole XIV as a yellow solid: LRMS for $C_9H_9IN_2O_2$ (M+H)$^+$ at m/z=305.

A solution of 7-iodo-2-methyl-5-nitro-2,3-dihydro-1H-indole XIV (4.75 g, 0.0156 mol) in methanol (150 mL) at 25° C. was treated with a solution of ammonium chloride (5.22 g, 0.0976 mol) in water (150 mL) and iron powder (3 g, 0.0534 mol). The mixture was heated to 100° C. under a nitrogen atmosphere for 6 h. The reaction mixture was filtered hot through a pad of celite and washed with hot methanol. The filtrate was concentrated in vacuo and the residue partitioned between methylene chloride and water. The layers were separated and the pH of the aqueous layer was adjusted to pH=10 with ammonium hydroxide. The aqueous layer was extracted with methylene chloride and the combined organic layers were dried over sodium sulfate, filtered, and concentrated in vacuo to a volume of 50 mL. The resulting solution was treated with a 4.0M aqueous hydrochloric acid solution in dioxane and then stirred at 25° C. for 1 h. The precipitate was collected by filtration and washed with methylene chloride and petroleum ether to afford 7-iodo-2-methyl-1H-indol-5-ylamine hydrochloride XV (4.37 g, 81%) as a gray solid: LRMS for freebase $C_9H_{11}IN_2$ (M+H)$^+$ at m/z=275.

A solution of 7-iodo-2-methyl-1H-indol-5-ylamine hydrochloride XV (4.3 g, 12.39 mmol) in methanol (200 mL) at 25° C. was treated with 2,3-dichloro-5,6-dicyano-1,4-benzoquinone (2.8 g, 12.39 mmol) in portions. The resulting dark solution was concentrated in vacuo and partitioned between water and methylene chloride, the pH was adjusted to 10 by the addition of with ammonium hydroxide, the organic layer separated and filtered and the aqueous layer extracted 3×100 mL with methylene chloride. The organic layers were combined, dried over magnesium sulfate and charcoal. The mixture was filtered and concentrated to 100 mL in volume before 20 mL of a 4.0 M HCL in dioxane solution was added. The resulting mixture was stirred at room temperature for 1 h and the precipitate formed was isolated by filtration, washed well with ether and dried to give 7-iodo-2-methyl-1H-indol-5-ylamine hydrochloride XVI (1.94 g, 58%) as a grey solid: LRMS for freebase $C_9H_9IN_2$ (M+H)$^+$ at m/z=273.

A solution of 7-iodo-2-methyl-1H-indol-5-ylamine hydrochloride XVII (1.9 g, 6.158 mmol) in N,N-dimethylformamide (30 mL) at 25° C. was treated with sodium dicyanamide (1.37 g, 15.397 mmol) and then warmed to 45° C. for 4 h. The resulting mixture filtered and concentrated in vacuo and the residue treated with water (20 mL). The resulting mixture was allowed to stand at 25° C. for 2.5 h during which time a solid formed. The solid was collected by filtration and washed with water, resuspended in methanol, filtered and dried to give N"-cyano-N-(7-iodo-2-methyl-1H-indol-5-yl)guanidine XVIII (0.88 g, 42%) as a light grey solid: LRMS for $C_{11}H_{10}IN_5$ (M–H)$^+$ at m/z=338.

A solution of N"-cyano-N-(7-iodo-2-methyl-1H-indol-5-yl)guanidine XVIII (0.86 g, 2.54 mmol) in 2-methoxyethyl ether (20 mL) was heated to 175° C. for 28 h. The reaction mixture was cooled to 25° C. and the solid formed was removed by filtration and washed with methanol. The filtrate was concentrated in vacuo and the residue triturated with methanol and ether to give a brown solid which was isolated by filtration and dried to give 6-iodo-8-methyl-7H-pyrrolo[3,2-f]quinazoline-1,3-diamine XIX (120 mg, 14%) as a brown solid: LRMS for $C_{11}H_{10}IN_5$ (M+H)$^+$ at m/z=340.

A solution of 6-iodo-8-methyl-7H-pyrrolo[3,2-f]quinazoline-1,3-diamine XIX (20 mg, 0.06 mmol) in ethylene glycol dimethyl ether (5.0 mL) and ethanol (2.5 mL) at 25° C. was treated with 2-thiopheneboronic acid (11 mg, 0.09 mmol), a 2 M aqueous sodium carbonate solution (2.5 mL), and tetrakis(triphenylphosphine)-palladium (0) (0.3 mg, 0.0026 mmol). The resulting mixture was heated to 80° C. for 3 h, cooled and pre-absorbed onto silica gel and purified by flash chromatography (Merck Silica gel 60, 230-400 mesh, 90/10/1 methylene chloride/methanol/ammonium hydroxide) followed by reversed phase HPLC (Zorbax 21.2×100 mmSB C18 column, 15 min 95/5 to 5/95 water/acetonitrile 0.075% TFA gradient) to afford 8-Methyl-6-thiophen-2-yl-7H-pyrrolo[3,2-f]quinazoline-1,3-diamine trifluoro-acetic acid salt XX (4 mg, 25%) as a lyophuilized solid, LRMS for freebase $C_{15}H_{13}N_5S_2$ (M+H)$^+$ at m/z=296.

In an analogous manner, there were obtained:

Example 114

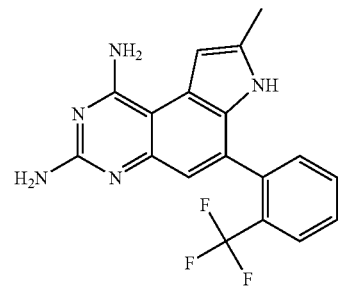

From 6-iodo-8-methyl-7H-pyrrolo[3,2-f]quinazoline-1,3-diamine 2-(trifluoromethylbenzene)boronic acid 8-Methyl-6-(2-trifluoromethyl-phenyl)-7H-pyrrolo[3,2-f]quinazoline-1,3-diamine as a lyophilized solid; LRMS for $C_{18}H_{14}F_3N_5$ (M+H)$^+$ at m/z=358.

Example 115

In vitro Inhibition of PTP1B

Enzymes

Human PTP1B (1-321) was cloned from a human cDNA library using conventional molecular biology techniques. The cDNA sequence was identical to the published human PTP1B sequence (Accession number M33689). The protein was expressed and purified from *E. coli* as described by Barford D. et.al, *J. Mol Biol* (1994) 239,726-730).

Example 116

PTPase Assays

The measurement of PTPase activity was carried out using one of two methods:

The first method for the measurement of PTP1B inhibitory activity a tyrosine phosphorylated peptide based on the amino acid sequence of insulin receptor tyrosine autophosphorylation site 1146 (TRDI(pY)E) was used as substrate. The reaction conditions were as follows:

PTP1B (0.5-2nM ) was incubated with compound for 15 min in buffer containing 37.5 mM Bis-Tris buffer pH 6.2, 140 mMNaCl, 0.05% BSA and 2 mM DTT. The reaction was started by the addition of 50 μM substrate. After 20 min at room temperature (22-25° C.) the reaction was stopped with KOH and the amount of free phosphate measured using Malachite Green as previously described. (Harder et al. 1994 *Biochem J.* 298; 395).

The second method was used for the measurement of general PTPase inhibitory activity across a panel of PTPases the substrate (6,8-difluoro-4-methylumbelliferyl phosphate (DiFMUP; from Molecular Probes) was used at the Km for each enzyme. The buffer conditions were identical as in the Malachite Green assay. The reaction was stopped with KOH. In this case the dephosphoryated product becomes fluorescent and the fluorescence read. (Excitiation: 360 mM/Emmission: 460 nM).

For kinetic experiments the same buffer conditions were used except that the reaction was started using enzyme and the reaction stopped after 10 minutes.

The $IC_{50}$ values (in μM) for the PTP1B inhibitory activity of the compounds in range of 5.20 μM to 96.3 μM. The most preferred compounds show an $IC_{50}$ of <30.0 μM.

Examples of the some compounds with its corresponding $IC_{50}$ values are

| Example | $IC_{50}$ (μM) |
|---|---|
| 2 | 23.79 |
| 4 | 89.52 |
| 6 | 29.22 |
| 8 | 24.11 |

Example 117

Glucose Uptake Assay the day before the assay the SKMC media was changed to high glucose DMEM, 25 mM Hepes, pH 7.0 and 2% Charcoal/dextran treated FBS for 19 hours.

On the morning of the assay, cells were starved for max. 2 hours in low glucose (5.5 mM glucose) DMEM 25 mM Hepes, pH 7.0 and 0.5% BSA. The starvation medium was removed and replaced with test medium (150 mMNaCl, 25mM Hepes, pH 7.0) containing either 1% DMSO, or test compound diluted in DMSO or Porcine Insulin to a final concentrations of 1, 0.1, 0.05, 0.01 and 0.01 μM. Each assay point was performed in triplicate. The cells were incubated for 45 min at 37° C. 10 μM Cytochalasin B (CB) was added to appropriate wells to stop the active glucose transport (i.e. GLUT 1 & 4). At this point 2-Deoxy-D(U-$^{14}$C) glucose (Amersham, Code CFB195, 200 uCi/ml) was added to all wells to a final concentration of 0.8 μCi/ml. The cells were incubated for an additional 45 minutes at 37° C. in an incubator. Cells were then very gently washed for three times in PBS (RT). The cells were then lysed with the addition of 0.05% NaOH solution for 20 min at RT. The lysate was transferred to a scintillation vial containing 5 ml of scintillation fluid and counted in a Beckman LS6500 Scintillation counter. Analysis of results: The counts obtained with CB (passive glucose transport values) were subtracted from every value obtained with PI (or compounds) in order to evaluate only active glucose transport. Fold increase was calculated by dividing values in the presence of PI (or compounds) by the value obtained in the presence of DMSO (control). Compounds were considered to be active when they increase glucose uptake at least 25% of the Porcine Insulin response at 0.05 μM.

Example 118

In vivo Inhibition of PTP1B: Effects of Compounds on Blood Glucose Levels in Mouse Model To measure the anti-diabetic effect compounds were tested in well established rodent in vivo models of type 2 diabetes and obesity.

Diet Induced Obese $C_{57}BL6/J$ Mice (DIO Mice)

Mice that have type 2 diabetes were be generated by maintaining them on a high fat diet for a 4-6 months (Diabetes vol. 37 Sept 1988). Male C57B16/J mice (age 3-4 weeks) were placed on high fat diet for 4-6 months. At this time, they were hyperglycemic and hyperinsulinemic and weighed 40-50 g. DIO mice (n=10) were weighed and fasted for a two hour period prior to oral treatment. Immediately prior to dosing a pre-dose blood glucose reading was taken by snipping off a portion of the tail and collecting blood from the tail vein. Mice were treated either with a single dose of compound (acute) or once a day for 5 days (sub-chronic). For the acute studies glucose was generally measured at 2 h, 4 h, 6 h, 8 h post treatment. Compounds were considered active if they showed a statistically significant ($p \leq 0,05$) glucose lowering (>15%) compared to the vehicle treated animals.

For sub-chronic (5 day) studies mice were dosed once a day by gavage as described above. On day five, glucose was measured prior to dosing (0 time) and 2 hours after dosing. Insulin and triglycerides were measured at 2 hour post dose. Compounds were considered active if they showed a statistically significant ($p \leq 0,05$) glucose, insulin and triglyceride lowering compared to the vehicle treated animals.

The invention claimed is:

1. A phenyl ring containing the compound of the formula:

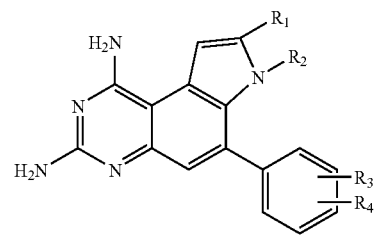

I-A wherein
  $R_1$ is selected from hydrogen and lower alkyl;
  $R_2$ is selected from the group consisting of hydrogen, lower alkyl,

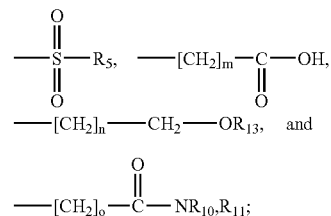

$R_3$ and $R_4$ are independently selected from the group consisting of hydrogen, lower alkyl, lower alkenyl, lower alkoxy, hydroxy lower alkyl, perfluoroloweralkyl, nitro, halo, lower alkanoyl, —N $R_5R_6$, $R_7S$—,

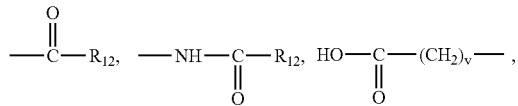

phenyl, hydroxy, perfluoroloweralkoxy, and phenoxy, or $R_3$ and $R_4$ when present on adjacent carbon atoms on the phenyl ring can be taken together to form a lower alkylenedioxy bridge or taken together with their adjacent carbon atoms to form an aromatic ring system fused to the phenyl ring, said aromatic ring system containing one or two aromatic rings with one of said rings being either an aromatic or heteroaromatic ring;

$R_5$ and $R_6$ are independently selected from hydrogen and lower alkyl;

$R_{12}$ is selected from the group consisting of hydrogen, benzyl, phenyl and lower alkyl;

$R_7$ is lower alkyl;

$R_{13}$ is selected from the group consisting of hydrogen, lower alkyl, benzyl and phenyl;

$R_{10}$, $R_{11}$ and $R_{12}$ are independently selected from hydrogen and lower alkyl; and m, n, o and v are independent integers selected from 0 to 4 or pharmaceutically acceptable salts thereof.

2. The compound of claim 1 wherein $R_1$ is hydrogen and $R_3$ and $R_4$ are substituted on adjacent carbon atoms and form a lower alkylene dioxy bridge and $R_2$ is selected from lower alkyl and hydrogen.

3. The compound of claim 2 wherein said compound is 6-benzo[1,3]dioxol-5-yl-7-methyl-7H-pyrrolo[3,2-f]quinazoline-1,3-diamine trifluoro-acetic acid salt.

4. The compound of claim 2 wherein $R_1$ is hydrogen and $R_3$ and $R_4$ are substituted on adjacent carbon atoms and taken together with their attached carbon atoms form a fused aromatic ring and $R_2$ is selected from hydrogen and lower alkyl.

5. The compound of claim 4 wherein said compound is 7-methyl-6-naphthalen-1-yl-7H-pyrrolo[3,2-f]quinazoline-1,3-diamine trifluoro-acetic acid salt.

6. The compound of claim 4 wherein said compound is 7-methyl-6-naphthalen-2-yl-7H-pyrrolo[3,2-f]quinazoline-1,3-diamine trifluoro-acetic acid salt.

7. The compound of claim 4 wherein said compound is 6-naphthalen-1-yl-7H-pyrrolo[3,2-f]quinazoline-1,3-diamine trifluoro-acetic acid salt.

8. The compound of claim 4 wherein said compound is 6-naphthalen-2-yl-7H-pyrrolo[3,2-f]quinazoline-1,3-diamine trifluoro-acetic acid salt.

9. The compound of claim 8 wherein said compound is 7-methyl-6-naphthalen-1-yl-7H-pyrrolo[3,2-f]quinazoline-1,3-diamine trifluoro-acetic acid salt.

10. The compound of claim 1 wherein
$R_3$ and $R_4$ are substituted on adjacent carbon atoms on the phenyl ring and taken together form a fused heteroaromatic ring; and
$R_1$ and $R_2$ are independently selected from hydrogen and lower alkyl.

11. The compound of claim 10 wherein said compound is 6-(3,5-6-Benzo[b]thiophen-7-yl-7-methyl-7H-pyrrolo[3,2-f]quinazoline-1,3-diamine trifluoro-acetic acid salt.

12. The compound of claim 1 wherein $R_3$ and $R_4$ are attached on adjacent carbon atoms on the phenyl ring and form a two membered ring system, one of said rings being a heteroaromatic ring and the other being an aromatic ring.

13. The compound of claim 12 wherein said compound is 7-methyl-6-phenoxathiin-4-yl-7H-pyrrolo[3,2-f]quinazoline-1,3-diamine trifluoro-acetic acid salt.

14. The compound of claim 1 wherein $R_1$ and $R_2$ are independently selected from hydrogen and lower alkyl, and $R_3$ and $R_4$ are independently selected from the group consisting of hydrogen, lower alkyl and lower alkenyl.

15. The compound of claim 14 wherein $R_4$ is lower alkenyl and $R_3$ is hydrogen.

16. The compound of claim 15 wherein said compound is 7-methyl-6-(4-vinyl-phenyl)-7H-pyrrolo[3,2-f]quinazoline-1,3-diamine trifluoro-acetic acid salt.

17. The compound of claim 14 wherein $R_4$ is selected from lower alkyl and hydrogen, and $R_3$ is lower alkenyl.

18. The compound of claim 17 wherein said compound 7-methyl-6-o-tolyl-7H-pyrrolo[3,2-f]quinazoline-1,3-diamine trifluoro-acetic acid salt.

19. The compound of claim 17 wherein said compound 6-(2,5-dimethyl-phenyl)-7-methyl-7H-pyrrolo[3,2-f]quinazoline-1,3-diamine trifluoro-acetic acid salt.

20. The compound of claim 17 wherein said compound is 7-methyl-6-m-tolyl-7H-pyrrolo[3,2-f]quinazoline-1,3-diamine trifluoro-acetic acid salt.

21. The compound of claim 17 wherein said compound 6-(4-ethyl-phenyl)-7H-pyrrolo[3,2-f]quinazoline-1,3-diamine trifluoro-acetic acid salt.

22. The compound of claim 17 wherein said compound 6-(4-tert-butyl-phenyl)-7H-pyrrolo[3,2-f]quinazoline-1,3-diamine trifluoro-acetic acid salt.

23. The compound of claim 1 wherein
$R_1$ and $R_2$ are independently selected from hydrogen and lower alkyl,
$R_3$ and $R_4$ are independently selected from hydrogen, halogen, trifluoroloweralkyl; and
one of $R_3$ and $R_4$ is other than hydrogen.

24. The compound of claim 23 wherein said compound is 6-(3,5-bis-trifluoromethyl-phenyl)-7H-pyrrolo[3,2-f]quinazoline-1,3-diamine.

25. The compound of claim 23 wherein said compound is 6-(4-fluoro-phenyl)-7H-pyrrolo[3,2-f]quinazoline-1,3-diamine trifluoro-acetic acid salt.

26. The compound of claim 23 wherein said compound is 6-(3-fluoro-phenyl)-7H-pyrrolo[3,2-f]quinazoline-1,3-diamine trifluoro-acetic acid salt.

27. The compound of claim 23 wherein said compound is 6-(2,4-dichloro-phenyl)-7H-pyrrolo[3,2-f]quinazoline-1,3-diamine trifluoro-acetic acid salt.

28. The compound of claim 23 wherein said compound is 6-(2-chloro-phenyl)-7H-pyrrolo[3,2-f]quinazoline-1,3-diamine trifluoro-acetic acid salt.

29. The compound of claim 23 wherein said compound is 6-(2-trifluoromethyl-phenyl)-7H-pyrrolo[3,2-f]quinazoline-1,3-diamine.

30. The compound of claim 23 wherein said compound is 6-(3-fluoro-phenyl)-7-methyl-7H-pyrrolo[3,2-f]quinazoline-1,3-diamine trifluoro-acetic acid salt.

31. The compound of claim 23 wherein said compound is 6-(2,4-dichloro-phenyl)-7-methyl-7H-pyrrolo[3,2-f]quinazoline-1,3-diamine trifluoro-acetic acid salt.

32. The compound of claim 23 wherein said compound is 7-methyl-6-(4-trifluoromethoxy-phenyl)-7H-pyrrolo[3,2-f]quinazoline-1,3-diamine trifluoro-acetic acid salt.

33. The compound of claim 23 wherein said compound is 6-(3,4-dichloro-phenyl)-7-methyl-7H-pyrrolo[3,2-f]quinazoline-1,3-diamine trifluoro-acetic acid salt.

34. The compound of claim 1 wherein
R$_1$ and R$_2$ are independently selected from hydrogen and lower alkyl;
R$_3$ is selected from hydrogen and halogen; and
R$_4$ is selected from the group consisting of halogen, nitro, lower alkoxy, phenoxy, hydroxy, hydroxyalkyl,

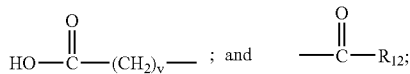

v is an integer selected from 0 to 4; and
R$_{12}$ is selected from hydrogen and lower alkyl.

35. The compound of claim 34 wherein R$_3$ is selected from hydrogen and halogen, and R$_4$ is selected from the group consisting of nitro, halogen, phenoxy, lower alkoxy, hydroxy and hydroxyalkyl.

36. The compound of claim 35 wherein said compound is 6-(3-ethoxy-phenyl)-7H-pyrrolo[3,2-f]quinazoline-1,3-diamine trifluoro-acetic acid salt.

37. The compound of claim 35 wherein said compound is 6-(3-nitro-phenyl)-7H-pyrrolo[3,2-f]quinazoline-1,3-diamine.

38. The compound of claim 35 wherein said compound is 6-(5-chloro-2-methoxy-phenyl)-7H-pyrrolo[3,2-f]quinazoline-1,3-diamine trifluoro-acetic acid salt.

39. The compound of claim 35 wherein said compound is [3-(1,3-diamino-7-methyl-7H-pyrrolo[3,2-f]quinazolin-6-yl)-phenyl]-methanol trifluoro-acetic acid salt.

40. The compound of claim 35 wherein said compound is 6-(5-fluoro-2-methoxy-phenyl)-7-methyl-7H-pyrrolo[3,2-f]quinazoline-1,3-diamine trifluoro-acetic acid salt.

41. The compound of claim 35 wherein said compound is 6-(2,6-difluoro-phenyl)-7-methyl-7H-pyrrolo[3,2-f]quinazoline-1,3-diamine trifluoro-acetic acid salt.

42. The compound of claim 35 wherein said compound is 7-methyl-6-(2-phenoxy-phenyl)-7H-pyrrolo[3,2-f]quinazoline-1,3-diamine trifluoro-acetic acid salt.

43. The compound of claim 34 wherein
R$_3$ is hydrogen, R$_4$ is

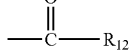

and
R$_{12}$ is selected from hydrogen and lower alkyl.

44. The compound of claim 43 wherein said compound is 3-(1,3-diamino-7H-pyrrolo[3,2-f]quinazolin-6-yl)-benzaldehyde.

45. The compound of claim 43 wherein said compound is 1-[3-(1,3-diamino-7-methyl-7H-pyrrolo[3,2-f]quinazolin-6-yl)-phenyl]-ethanone trifluoro-acetic acid salt.

46. The compound of claim 34 wherein
R$_3$ and R$_4$ are independently selected from hydrogen and

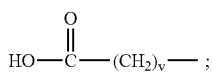

v is as above;
R$_1$ and R$_2$ are selected from hydrogen and lower alkyl; and
one of R$_3$ and R$_4$ is other than hydrogen.

47. The compound of claim 46 wherein said compound is 3-[2-(1,3-diamino-7H-pyrrolo[3,2-f]quinazolin-6-yl)-phenyl]-propionic acid.

48. The compound of claim 46 wherein said compound is [3-(1,3-diamino-7H-pyrrolo[3,2-f]quinazolin-6-yl)-phenyl]-acetic acid.

49. The compound of claim 46 wherein said compound is [4-(1,3-diamino-7H-pyrrolo[3,2-f]quinazolin-6-yl)-phenyl]-acetic acid.

50. The compound of claim 46 wherein said compound is 3-[3-(1,3-diamino-7H-pyrrolo[3,2-f]quinazolin-6-yl)-phenyl]-propionic acid.

51. The compound of claim 1 wherein
R$_1$ and R$_2$ are independently selected from hydrogen and lower alkyl;
R$_3$ and R$_4$ are selected from the group consisting of hydrogen, 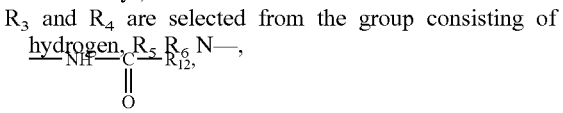

and
R$_7$S—;
R$_5$ and R$_6$ are independently selected from hydrogen and lower alkyl;
R$_7$ is lower alkyl; and
one of R$_3$ and R$_4$ is other than hydrogen.

52. The compound of claim 51 wherein said compound is 6-(3-amino-phenyl)-7-methyl-7H-pyrrolo[3,2-f]quinazoline-1,3-diamine trifluoro-acetic acid salt.

53. The compound of claim 51 wherein said compound is 6-(4-ethylsulfanyl-phenyl)-7-methyl-7H-pyrrolo[3,2-f]quinazoline-1,3-diamine trifluoro-acetic acid salt.

54. The compound of claim 1 wherein
R$_2$ is selected from

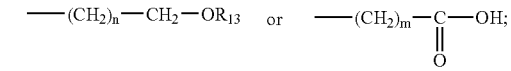

R$_{13}$ is selected from the group consisting of hydrogen, phenyl, benzyl and lower alkyl; and
n is an integer from 0 to 4.

55. The compound of claim 54 wherein said compound is 2-[1,3-diamino-6-(2-trifluoromethyl-phenyl)-pyrrolo[3,2-f]quinazolin-7-yl]-ethanol trifluoro-acetic acid salt.

56. The compound of claim 55 wherein said compound is 7-(2-benzyloxy-ethyl)-6-(2-trifluoromethyl-phenyl)-7H-pyrrolo[3,2-f]quinazoline-1,3-diamine trifluoro-acetic acid salt.

57. The compound of claim 55 wherein said compound is [1,3-diamino-6-(2-trifluoromethyl-phenyl)-pyrrolo[3,2-f]quinazolin-7-yl]-acetic acid trifluoro-acetic acid salt.

58. The compound of claim 1 wherein
R$_2$ is

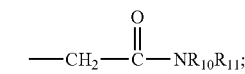

R$_{10}$ and R$_{11}$, are independently selected from hydrogen and lower alkyl.

59. The compound of claim 58 wherein said compound is 2-[1,3-diamino-6-(3-methoxy-phenyl)-pyrrolo[3,2-f]quinazolin-7-yl]—N,N-diethyl-acetamide.

* * * * *

UNITED STATES PATENT AND TRADEMARK OFFICE
CERTIFICATE OF CORRECTION

PATENT NO. : 7,262,297 B2  Page 1 of 1
APPLICATION NO. : 10/836507
DATED : August 28, 2007
INVENTOR(S) : Steven Joseph Berthel et al.

It is certified that error appears in the above-identified patent and that said Letters Patent is hereby corrected as shown below:

In Claim 1 at Column 58, line 34, please delete - "phenyl ring containing the"

Signed and Sealed this

Seventeenth Day of June, 2008

JON W. DUDAS
*Director of the United States Patent and Trademark Office*